United States Patent
David et al.

(10) Patent No.: US 7,351,267 B2
(45) Date of Patent: Apr. 1, 2008

(54) SYMMETRICAL DIAZO COMPOUNDS COMPRISING 2-IMIDAZOLIUM GROUPS AND A NON-CATIONIC LINKE, COMPOSITIONS COMPRISING THEM, METHOD OF COLORING, AND DEVICE

(75) Inventors: Hervé David, la Varenne Saint Hilaire (FR); Andrew Greaves, Montevrain (FR); Nicolas Daubresse, la Celles St Cloud (FR)

(73) Assignee: L'Oreal S.A., Paris (FR)

( * ) Notice: Subject to any disclaimer, the term of this patent is extended or adjusted under 35 U.S.C. 154(b) by 273 days.

(21) Appl. No.: 11/300,300

(22) Filed: Dec. 15, 2005

(65) Prior Publication Data

US 2006/0156477 A1 Jul. 20, 2006

Related U.S. Application Data

(60) Provisional application No. 60/646,977, filed on Jan. 27, 2005.

(51) Int. Cl.
*A61K 7/13* (2006.01)
(52) U.S. Cl. ...................... 8/405; 8/406; 8/407; 8/435; 8/437; 8/466; 8/570; 534/608; 548/300.1
(58) Field of Classification Search .................. 8/405, 8/406, 407, 435, 437, 466, 570; 534/608; 548/300.1
See application file for complete search history.

(56) References Cited

U.S. PATENT DOCUMENTS

| | | |
|---|---|---|
| 3,151,106 A | 9/1964 | Tsang et al. |
| RE30,199 E | 1/1980 | Rose et al. |
| 4,557,732 A | 12/1985 | Hähnke et al. |
| 4,823,985 A | 4/1989 | Grollier et al. |
| 5,151,106 A | 9/1992 | Bhaumik et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,733,343 A | 3/1998 | Möckli |
| 5,766,576 A | 6/1998 | Löwe et al. |
| 5,792,221 A | 8/1998 | Lagrange et al. |
| 5,852,179 A | 12/1998 | Dado |
| 5,888,252 A | 3/1999 | Möckli |
| 6,099,592 A | 8/2000 | Vidal et al. |
| 6,099,593 A | 8/2000 | Terranova et al. |
| 6,270,533 B1 | 8/2001 | Genet et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,824,570 B2 | 11/2004 | Vidal et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |

(Continued)

FOREIGN PATENT DOCUMENTS

DE 23 59 399 A1 6/1975

(Continued)

OTHER PUBLICATIONS

STIC Search Report dated Jun. 19, 2007.*
English Language Derwent Abstract for DE 38 43 892 A1, 1990.
English Language Derwent Abstract for EP 0 770 375 B1, 1997.
English Language Derwent Abstract for JP 05-163124, 1993.
English Language Derwent Abstract for JP 2-19576, 1990.
French Search Report for French Patent Application No. FR 04/52998, priority document for co-pending U.S. Appl. No. 11/300,314, Aug. 3, 2005.

(Continued)

*Primary Examiner*—Eisa Elhilo
(74) *Attorney, Agent, or Firm*—Finnegan, Henderson, Farabow, Garrett & Dunner, LLP

(57) ABSTRACT

The present disclosure relates to symmetrical cationic diazo compounds of formula (I) below, their resonance forms, and also their acid addition salts and their solvates:

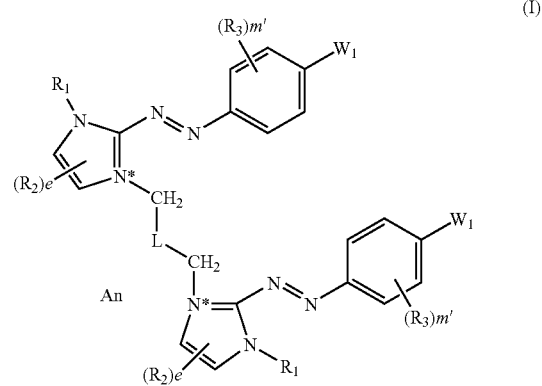

wherein $W_1$ radicals, which are identical, are chosen from a halogen atom, or an —$NR_4$-Ph-$NR_5R_6$, —$NR_4$-Ph-$OR_7$, —O-Ph-$OR_7$ or —O-Ph-$NR_5R_6$ group or else an —$NR_5R_6$ or —$OR_7$ group with certain provisos;

L, a non-cationic linker connecting the two identical azo chromophores, is chosen from a covalent bond; an optionally substituted $C_1$-$C_{40}$ alkyl radical optionally interrupted by a (hetero)cycle, the alkyl radical being optionally interrupted by at least one heteroatom or group comprising at least one heteroatom or an optionally substituted phenyl radical.

The disclosure further relates to dyeing compositions comprising such compounds as a direct dye in a medium appropriate for the dyeing of keratin fibers, and also to a method of coloring keratin fibers that employs this composition, and a device comprising a plurality of compartments.

27 Claims, No Drawings

U.S. PATENT DOCUMENTS

| | | |
|---|---|---|
| 7,001,436 B2 | 2/2006 | Vidal et al. |
| 7,022,143 B2 | 4/2006 | Vidal et al. |
| 2002/0095732 A1 | 7/2002 | Kravtchenko et al. |
| 2002/0187435 A1 | 12/2002 | Manakli et al. |
| 2003/0084516 A9 | 5/2003 | Kravtchenko et al. |
| 2002/0050013 A1 | 6/2003 | Vidal et al. |
| 2003/0106169 A1 | 6/2003 | Vidal et al. |
| 2004/0093675 A1 | 5/2004 | Vidal et al. |
| 2004/0093676 A1 | 5/2004 | Vidal et al. |
| 2004/0107513 A1 | 6/2004 | Vidal et al. |
| 2004/0127692 A1 | 7/2004 | David et al. |
| 2004/0143911 A1 | 7/2004 | Vidal |
| 2004/0168263 A1 | 9/2004 | Vidal |
| 2004/0187225 A1 | 9/2004 | Vidal et al. |
| 2004/0187228 A1 | 9/2004 | LaGrange |
| 2004/0200009 A1 | 10/2004 | Vidal |
| 2004/0221399 A1 | 11/2004 | Cotteret et al. |
| 2004/0244123 A1 | 12/2004 | Vidal et al. |
| 2004/0244124 A1 | 12/2004 | Plos et al. |
| 2005/0008594 A1 | 1/2005 | Plos et al. |
| 2005/0039268 A1 | 2/2005 | Plos et al. |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 770 375 B1 | 5/1997 |
| EP | 0 714 954 B1 | 9/2002 |
| EP | 1 428 505 A1 | 6/2004 |
| EP | 1 433 474 A1 | 6/2004 |
| EP | 1 219 683 B1 | 7/2004 |
| EP | 1 464 327 A1 | 10/2004 |
| FR | 2 586 913 A1 | 3/1987 |
| FR | 2 692 572 A1 | 12/1993 |
| FR | 2 733 749 A1 | 11/1996 |
| FR | 2 750 048 A1 | 12/1997 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 | 10/2002 |
| FR | 2 825 625 | 12/2002 |
| FR | 2 825 702 A1 | 12/2002 |
| FR | 2 829 926 A1 | 3/2003 |
| FR | 2 844 269 A1 | 3/2004 |
| GB | 1 026 978 | 4/1966 |
| GB | 1 153 196 | 5/1969 |
| JP | 02-19576 | 1/1990 |
| JP | 05-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 99/03834 A2 | 1/1999 |
| WO | WO 02/30374 A1 | 4/2002 |
| WO | WO 02/078596 | * 10/2002 |
| WO | WO 02/078596 A2 | 10/2002 |
| WO | WO 02/078660 A1 | 10/2002 |
| WO | WO 02/080869 A2 | 10/2002 |
| WO | WO 02/100366 A2 | 12/2002 |
| WO | WO 02/100368 A1 | 12/2002 |
| WO | WO 02/100369 A2 | 12/2002 |
| WO | WO 02/100834 A1 | 12/2002 |
| WO | WO 2004/083312 A2 | 9/2004 |

OTHER PUBLICATIONS

French Search Report for French Patent Application No. FR 04/52999, priority document for co-pending U.S. Appl. No. 11/300,271, Aug. 1, 2005.

French Search Report for French Patent Application No. FR 04/53000, priority document for co-pending U.S. Appl. No. 11/300,284, Aug. 3, 2005.

French Search Report for French Patent Application No. FR 04/53002, priority document for co-pending U.S. Appl. No. 11/300,300, (present case), Sep. 16, 2005.

French Search Report for French Patent Application No. FR 04/53006, priority document for co-pending U.S. Appl. No. 11/300,432, Sep. 19, 2005.

French Search Report for French Patent Application No. FR 04/53008, priority document for co-pending U.S. Appl. No. 11/300,303, Aug. 24, 2005.

French Search Report for French Patent Application No. FR 04/53005, priority document for co-pending U.S. Appl. No. 11/300,512, Aug. 23, 2005.

Co-pending U.S. Appl. No. 11/300,314, filed Dec. 15, 2005, by inventors David et al.

Co-pending U.S. Appl. No. 11/300,271, filed Dec. 15, 2005, by inventors David et al.

Co-pending U.S. Appl. No. 11/300,284, filed Dec. 15, 2005, by inventors David et al.

Co-pending U.S. Appl. No. 11/300,432, filed Dec. 15, 2005, by inventors David et al.

Co-pending U.S. Appl. No. 11/300,303, filed Dec. 15, 2005, by inventors David et al.

Co-pending U.S. Appl. No. 11/300,512, filed Dec. 15, 2005, by inventors David et al.

E. Buncel et al.; "Studies Of Azo And Azoxy Dyestuffs—16† Investigations Of The Protonation And Tautomeric Equilibria Of 4-(p'-Hydroxyphenylazo)Pyridine And Related Substrates;" *Tetrahedron*;(1983); pp. 1091-1101; vol. 39, No. 7.

I. Onyido et al.; "Heteroaromatic Azo-Activated Nucleophilip Substitutions. The Reaction of 4-(p-Methoxyphenylazo)Pyridinium Methiodide With Piperidine In Dimethyl Sulphoxide;" *Heterocycles*; (1987); pp. 313-317; vol. 26, No. 2.

M. H. Habibi et al., "Efficient Catalytic Oxidation Of Primary Aromatic Amines To Azo Derivatives By Manganese(III) Tetraphenylporphyin†," *J. Chem. Research* (S), (1998), pp. 648-649, vol. 10.

X.-Y. Wang et al.; "The Preparation Of Symmetrical Azobenzenes From Anilines By Phase Transfer Catalyzed Method;" *Synthetic Communications*; (1999); pp. 2271-2276; vol. 29, No. 13.

* cited by examiner

SYMMETRICAL DIAZO COMPOUNDS COMPRISING 2-IMIDAZOLIUM GROUPS AND A NON-CATIONIC LINKE, COMPOSITIONS COMPRISING THEM, METHOD OF COLORING, AND DEVICE

This application claims benefit of U.S. Provisional Application No. 60/646,977, filed Jan. 27, 2005, the contents of which are incorporated herein by reference. This application also claims benefit of priority under 35 U.S.C. § 119 to French Patent Application No. 04 53002, filed Dec. 15, 2004, the contents of which are also incorporated herein by reference.

The present disclosure relates to symmetrical cationic diazo compounds comprising 2-imidazolium groups and a non-cationic linker, dyeing compositions comprising such compounds as a direct dye in a medium appropriate for the dyeing of keratin fibers, a method of coloring keratin fibers that employs this composition, and a device having a plurality of compartments.

It is known practice to dye keratin fibers, for example, human keratin fibers such as the hair, with dyeing compositions comprising direct dyes. These compounds may be colored and coloring molecules having an affinity for the fibers. It is known practice, for example, to use direct dyes chosen from nitrobenzene type, anthraquinone dyes, nitropyridines and dyes of azo, xanthene, acridine, azine and triarylmethane dyes.

These dyes may be applied to the fibers, optionally in the presence of an oxidizing agent if a simultaneous fiber lightening effect is desired. When the leave-in time has elapsed, the fibers may be rinsed, optionally washed, and dried.

The colorations which result from the use of direct dyes are temporary or semi-permanent colorations, because the nature of the interactions which bind the direct dyes to the keratin fiber, and their desorption from the surface and/or the core of the fiber, are responsible for their relatively low tinctorial strength and relatively poor wash resistance and/or perspiration resistance.

It is known from European Patent Application No. 1377263 to employ particular direct cationic diazo dyes comprising two cationic heterocyclic groups. These compounds, although representing an advance in the art, give dyeing results which nevertheless remain capable of improvement.

For the purposes of the present disclosure, and in the absence of any indication otherwise:

an alkyl(ene) radical or the alkyl(ene) moiety of a radical is linear or branched.

an alkyl(ene) radical or the alkyl(ene) moiety of a radical is said to be substituted when it comprises at least one substituent chosen from the following groups:

hydroxyl groups, $C_1$-$C_4$ alkoxy and $C_2$-$C_4$ (poly)hydroxyalkoxy groups, amino groups substituted by one or two identical or different $C_1$-$C_4$ alkyl groups which optionally carry at least one group chosen from hydroxyl and $C_1$-$C_2$ alkoxy groups, it being possible for the alkyl radicals to form, with the nitrogen atom to which they are attached, a heterocycle comprising 5 or 7 ring members which is saturated or unsaturated, is optionally aromatic, is optionally substituted and comprises optionally at least one other heteroatom different or not from nitrogen, an alkylcarbonylamino radical (R'CO—NR—) wherein the radical R is chosen from hydrogen atom and $C_1$-$C_4$ alkyl radicals and the radical R' is chosen from $C_1$-$C_2$ alkyl radicals, an alkylsulphonyl radical (R—$SO_2$—) wherein the radical R is chosen from $C_1$-$C_4$ alkyl radicals, an alkylsulphinyl radical (R—SO—) wherein the radical R is chosen from $C_1$-$C_4$ alkyl radicals, an alkylcarbonyl radical (R—CO—) wherein the radical R is chosen from $C_1$-$C_4$ alkyl radicals.

An aromatic or non-aromatic, saturated or unsaturated (hetero)cyclic radical, or the aromatic or non-aromatic, saturated or unsaturated (hetero)cyclic moiety of a radical, is said to be substituted when it comprises at least one substituent, which, in at least one embodiment, may be carried by a carbon atom, chosen from:

an optionally substituted $C_1$-$C_{16}$, for example, optionally substituted $C_1$-$C_8$, alkyl radicals;

halogen atoms such as chlorine, fluorine, and bromine;

hydroxyl groups;

$C_1$-$C_4$ alkoxy radicals and $C_2$-$C_4$ (poly)hydroxyalkoxy radicals;

amino radicals;

amino radicals substituted by one or two identical or different $C_1$-$C_4$ alkyl radicals which optionally carry at least one group chosen from hydroxyl, amino, $C_1$-$C_4$ (mono- or di-)alkylamino, and $C_1$-$C_2$ alkoxy groups, it being possible for the two alkyl radicals, with the nitrogen atom to which they are attached, to form a heterocycle comprising from 1 to 3 heteroatoms, for example, from 1 or 2 heteroatoms, chosen from N, O and S, the heterocycle comprising 5 to 7 ring members, and being saturated or unsaturated and aromatic or non-aromatic, and optionally substituted. In at least one embodiment, the heteroatom(s) may be nitrogen;

alkylcarbonylamino radicals (R'CO—NR—) wherein the radical R is chosen from hydrogen and $C_1$-$C_4$ alkyl radicals and the radical R' is chosen from $C_1$-$C_2$ alkyl radicals;

aminocarbonyl radicals (($R)_2$N—CO—) wherein the radicals R, which are identical or different, are chosen from hydrogen and $C_1$-$C_4$ alkyl radicals;

alkylsulphonylamino radicals (R'$SO_2$—NR—) wherein the radical R is chosen from hydrogen and $C_1$-$C_4$ alkyl radicals and the radical R' is chosen from $C_1$-$C_4$ alkyl radicals and phenyl radicals; and aminosulphonyl radicals (($R)_2$N—$SO_2$—) wherein the radicals R, which are identical or different, are chosen from hydrogen and $C_1$-$C_4$ alkyl radicals.

The compounds according to the present disclosure are termed symmetrical when there exists a plane of symmetry perpendicular to the linker L.

According to the present invention, where the different groups forming part of the structure of the compounds according to the present disclosure are substituted, the person skilled in the art will choose the substituents such that the symmetry of the molecule is respected.

It is desirable to provide direct dyes which do not exhibit the drawbacks of existing direct dyes.

Accordingly, the present disclosure provides symmetrical cationic diazo compounds of formula (I) below, their resonance forms, and their acid addition salts, and/or their solvates:

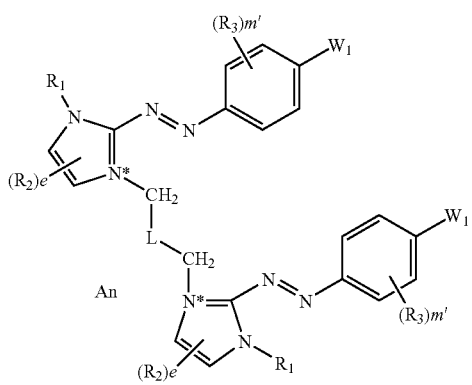

(I)

wherein formula:
the radicals $R_1$, which may be identical or different, are chosen from:
optionally substituted $C_1$-$C_4$ alkyl radicals;
optionally substituted phenyl radicals; and
optionally substituted benzyl radicals;

the radicals $R_2$, which may be identical or different, are chosen from:
optionally substituted $C_1$-$C_{16}$ alkyl radicals optionally interrupted by at least one heteroatom and/or by at least one group comprising at least one heteroatom chosen from, for example, oxygen, nitrogen, sulphur, —CO—, —SO$_2$— or combinations thereof, the alkyl radicals being further optionally substituted by at least one group chosen from thio (—SH), $C_1$-$C_4$ thioalkyl; $C_1$-$C_4$ alkylsulphinyl, and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ radicals,
alkylcarbonyl radicals (R—CO—) wherein R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms, for example, from 1 to 2 heteroatoms, chosen from N, O and S, and comprising 5 to 7 ring members, which is saturated or unsaturated, aromatic or non-aromatic and optionally substituted. In at least one embodiment, the heteroatom(s) may be nitrogen;
alkylcarbonylamino groups (RCO—NR'—) wherein the radical R is chosen from $C_1$-$C_4$ alkyl radicals and the radical R' is chosen from hydrogen, and $C_1$-$C_4$ alkyl radicals;
aminocarbonyl groups ((R)$_2$N—CO—) wherein the radicals R, which may be identical or different, are independently chosen from hydrogen and $C_1$-$C_4$ alkyl radicals;
ureido groups (N(R)$_2$—CO—NR'—) wherein the radicals R and R', which may be identical or different, are independently chosen from hydrogen and $C_1$-$C_4$ alkyl radicals;
aminosulphonyl groups ((R)$_2$N—SO$_2$—) wherein the radicals R, which may be identical or different, are independently chosen from hydrogen and $C_1$-$C_4$ alkyl radicals;
alkylsulphonylamino groups (RSO$_2$—NR'—) wherein R is chosen from $C_1$-$C_4$ alkyl radicals and R' is chosen from hydrogen and $C_1$-$C_4$ alkyl radicals;
optionally substituted aryl radicals;
optionally substituted ($C_1$-$C_4$ alkyl)aryl radicals;
alkylsulphinyl groups (R—SO—) wherein R is chosen from $C_1$-$C_4$ alkyl radicals;
alkylsulphonyl groups (R—SO$_2$—) wherein R is chosen from $C_1$-$C_4$ alkyl radicals;
nitro groups;
cyano groups;
halogen atoms, such as chlorine and fluorine;
thio groups (HS—); and
alkylthio groups (RS—) wherein the radical R is chosen from optionally substituted $C_1$-$C_4$ alkyl radicals;
when e is 2, the two radicals $R_2$ may optionally form, with the carbon atoms to which they are attached, a secondary, aromatic or non-aromatic ring, comprising 5 or 6 ring members, which is optionally substituted by at least one identical or non-identical group chosen from hydroxyl, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

e is an integer from 0 to 2; when e is less than 2, the one or more unsubstituted carbon atoms of the heterocycle carry a hydrogen atom, the radicals $R_3$, which may be identical or different are independently chosen from:
optionally substituted $C_1$-$C_{16}$ alkyl radicals optionally interrupted by at least one heteroatom or by at least one group comprising at least one heteroatom chosen, for example, from oxygen, nitrogen, sulphur, —CO—, —SO$_2$— or combinations thereof,
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals;
alkylcarbonyl radicals (R—CO—) wherein R is chosen from $C_1$-$C_4$ alkyl radicals;
amino groups;
amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms, for example, from 1 to 2 heteroatoms, chosen from N, O and S, and comprising 5 to 7 ring members, which is saturated or unsaturated, aromatic or non-aromatic and optionally substituted. In at least one embodiment, the heteroatom(s) may be nitrogen;

alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;

aminocarbonyl groups ((R)$_2$N—CO—) wherein the radicals R, which may be identical or different are independently chosen from hydrogen and $C_1$-$C_4$ alkyl radicals;

ureido groups (N(R)$_2$—CO—NR'—) wherein the radicals R and R', which may be identical or different are independently chosen from hydrogen and $C_1$-$C_4$ alkyl radicals;

aminosulphonyl groups ((R)$_2$N—SO$_2$—) wherein the radicals R, which may be identical or different are independently chosen from hydrogen and $C_1$-$C_4$ alkyl radicals;

alkylsulphonylamino groups (RSO$_2$—NR'—) wherein the radicals R and R', which may be identical or different are independently chosen from hydrogen and $C_1$-$C_4$ alkyl radical;

thio groups (HS—);

alkylthio groups (RS—) wherein the radical R is chosen from $C_1$-$C_4$ alkyl radicals;

alkylsulphinyl groups (R—SO—) wherein R is chosen from $C_1$-$C_4$ alkyl radicals;

alkylsulphonyl groups (R—SO$_2$—) wherein R is chosen from $C_1$-$C_4$ alkyl radicals;

nitro groups;

cyano groups; and halogen atom, such as chlorine and fluorine;

when m' is greater than or equal to 2, two adjacent radicals $R_3$ may form, with the carbon atoms to which they are attached, a secondary, aromatic and non-aromatic ring, comprising 6 ring members, which is optionally substituted by at least one group chosen from: hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group, m' is an integer from 0 to 4; when m' is less than 4, the unsubstituted carbon atom(s) of the heterocycle carry a hydrogen atom;

the radicals $W_1$, which may be identical or different, are independently chosen from:
hydrogen,
halogen atoms chosen from bromine, chlorine and fluorine. In at least one embodiment, the halogen atoms may be chosen from chlorine and fluorine,
—NR$_4$-Ph-NR$_5$R$_6$, —NR$_4$-Ph-OR$_7$, —O-Ph-OR$_7$ and —O-Ph-NR$_5$R$_6$ groups; wherein:
$R_4$ and $R_7$, which may be identical or different, are chosen from hydrogen, optionally substituted $C_1$-$C_{20}$, for example, optionally substituted, $C_1$-$C_{16}$, alkyl radicals, optionally substituted $C_1$-$C_3$ aralkyl radicals and optionally substituted phenyl radicals;
$R_5$ and $R_6$, which may be identical or different, are chosen from hydrogen, optionally substituted $C_1$-$C_{20}$, for example, optionally substituted $C_1$-$C_{16}$, alkyl radicals, optionally substituted phenyl radicals, optionally substituted $C_1$-$C_3$ aralkyl radicals and alkylcarbonyl radicals (R—CO—) wherein R is chosen from $C_1$-$C_4$ alkyl radicals;
$R_5$ and $R_6$ may optionally form, with the nitrogen atom to which they are attached, a heterocycle comprising from 1 to 3 heteroatoms, for example, from 1 or 2 heteroatoms, chosen from N, O and S and comprising 5 to 7 ring members, which is saturated or unsaturated, aromatic or non-aromatic and optionally substituted. In at least one embodiment, the heteroatom(s) may be nitrogen;

Ph is chosen from optionally substituted phenyl radicals;

group —NR$_5$R$_6$ wherein $R_5$ and $R_6$ independently of one another form, with the carbon atom of the aromatic ring adjacent to that to which —NR$_5$R$_6$ is attached, may form a 5- or 6-membered saturated heterocycle; and a group —OR$_7$ or —NR$_5$R$_6$ as defined above, when two adjacent radicals $R_3$ form an optionally substituted 6-membered aromatic secondary ring; this substitution may additionally be a radical —NR$_4$-Ph, —NR$_4$-Ph-OR$_7$ and —NR$_4$-Ph-NR$_5$R$_6$ radicals. This means that it is possible, for example, to have:

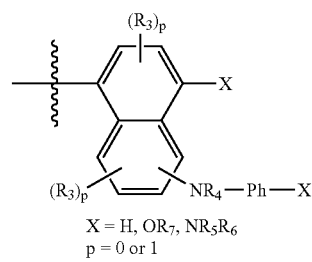

X = H, OR$_7$, NR$_5$R$_6$
p = 0 or 1

L, a non-cationic linker connecting the two identical azo chromophores, may be chosen from:

covalent bonds;

optionally substituted $C_1$-$C_{40}$, for example, optionally substituted $C_1$-$C_{20}$ alkyl radicals optionally interrupted by a saturated or unsaturated, aromatic or non-aromatic (hetero)cycle comprising from 3 to 7 ring members which is optionally substituted and optionally fused, the alkyl radicals being optionally interrupted by at least one entity chosen from heteroatom and group comprising at least one heteroatom, such as oxygen, nitrogen, sulphur, —CO—, —SO$_2$— or combinations thereof, with the proviso that the linker L does not comprising an azo, nitro, nitroso or peroxo bond; and optionally substituted phenyl radicals.

the electroneutrality of the compound of formula (I) being ensured by at least one identical or non-identical, cosmetically acceptable anions An.

Also disclosed herein are dyeing compositions comprising compounds of the formula (I), or their acid addition salts, as direct dyes in a medium appropriate for the dyeing of keratin fibers.

Further disclosed herein is a method of coloring keratin fibers which comprises contacting a composition according to the invention with fibers, which are dry or wet, for a time sufficient to give the desired effect.

Still further disclosed herein is a device comprising a plurality of compartments and comprising in a first compartment a composition according to the present disclosure and in a second compartment an oxidizing composition.

The present inventors have discovered that the compounds of formula (I) as defined above may exhibit effective resistance to external agents such as shampoos, and may do so even when the keratin fiber is sensitized.

Other characteristics and advantages of embodiments of the present disclosure will appear more clearly from reading the description and the examples which will be presented below.

In the present disclosure below, and in the absence of any indication otherwise, the end-points delimiting a range of values are included in that range.

As indicated above, the disclosure first provides compounds corresponding to the aforementioned formula (I).

According to at least one embodiment of the present disclosure, in the compounds of formula (I) the identical radicals $R_1$, may be chosen from:

$C_1$-$C_4$ alkyl radicals optionally substituted by at least one radical chosen from hydroxyl, $C_1$-$C_2$ alkoxy, amino and $C_1$-$C_2$ (di)alkylamino radicals; and optionally substituted benzyl radicals.

In one embodiment of the present disclosure, the identical groups $R_1$ may be chosen from methyl, ethyl, 2-hydroxyethyl, 2-methoxyethyl and benzyl radicals.

The radicals $R_2$, which may be identical or different, may be chosen from:

halogen atoms, for example, chlorine and fluorine;

$C_1$-$C_4$ alkyl radicals optionally substituted by at least one radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl and $C_1$-$C_4$ thioalkyl radicals;

phenyl radicals optionally substituted by at least one radical chosen from hydroxyl, $C_1$-$C_2$ alkoxy, $C_2$-$C_4$ (poly)hydroxyalkoxy, amino and $C_1$-$C_2$ (di)alkylamino radicals and halogen atoms, for example, chlorine and fluorine;

$C_1$-$C_4$ alkoxy radicals;

$C_1$-$C_4$ alkylsulphonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylsulphonylamino radicals ($RSO_2N$—) wherein the radical R is chosen from $C_1$-$C_4$ alkyl radicals;

aminosulphonyl radicals (($R)_2NSO_2$—) wherein the radicals R, which may be identical or different are independently chosen from hydrogen and $C_1$-$C_4$ alkyl radicals;

alkylthio radicals (RS—) wherein the radical R is chosen from $C_1$-$C_4$ alkyl radicals;

alkylsulphinyl radicals (RSO—) wherein the radical R is chosen from $C_1$-$C_4$ alkyl radicals;

alkylsulphonyl radicals (R—$SO_2$—) wherein the radical R is chosen from $C_1$-$C_4$ alkyl radicals; and alkylcarbonylamino radicals (RCONR'—) wherein the radical R is chosen from hydrogen and $C_1$-$C_4$ alkyl radicals and the radical R' is chosen from hydrogen and $C_1$-$C_4$ alkyl radicals.

In another embodiment of the present disclosure, the radicals $R_2$, which may be identical or different, may be independently chosen from a methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, methoxy, ethoxy and phenyl radicals.

In yet another embodiment of the present disclosure, the two radicals $R_2$ may optionally form, with the carbon atoms to which they are attached, a secondary, 6-membered, aromatic ring optionally substituted by at least one identical or different group chosen from hydroxyl groups, $C_1$-$C_4$ alkyl groups, $C_1$-$C_4$ alkoxy groups, amino groups, and $C_1$-$C_4$ (di)alkylamino groups which are identical or different and optionally carry at least one group chosen from hydroxyl or methylcarbonylamino groups.

In accordance with this embodiment of the present disclosure, the two radicals $R_2$ may optionally form, with the carbon atoms to which they are attached, a secondary, 6-membered, aromatic ring optionally substituted by at least one substituent chosen from hydroxyl, methoxy, ethoxy, amino, methylcarbonylamino, 2-hydroxyethylamino, dimethylamino and (di)-2-hydroxyethylamino substituents.

According to at least one embodiment of the present disclosure, the radicals $R_3$, these radicals, which may be identical or different, are independently chosen from:

optionally substituted $C_1$-$C_{16}$, for example, optionally substituted $C_1$-$C_8$, alkyl radicals;

halogen atoms, for example, chlorine and fluorine;

hydroxyl groups;

$C_1$-$C_2$ alkoxy radicals;

$C_2$-$C_4$ (poly)hydroxyalkoxy radicals;

amino radicals;

amino radicals substituted by one or two identical or different $C_1$-$C_4$ alkyl radicals which optionally carry at least one group chosen from hydroxyl groups and $C_1$-$C_4$ alkoxy radicals, it being possible for the two alkyl radicals to form, with the nitrogen to which they are attached, a heterocycle comprising from 1 to 3 heteroatoms, for example, from 1 or 2 heteroatoms, chosen from N, O and S, the heterocycle comprising 5 to 7 ring members, being saturated or unsaturated, aromatic or non-aromatic, and optionally substituted. In at least one embodiment the heteroatom(s) may be nitrogen;

alkylcarbonylamino radicals (RCO—NR'—) wherein the radical R is chosen from $C_1$-$C_4$ alkyl radicals and the radical R' is chosen from hydrogen and $C_1$-$C_4$ radicals;

alkylsulphonylamino radicals (R'$SO_2$—NR—) wherein the radical R is chosen from hydrogen and $C_1$-$C_4$ alkyl radicals and the radical R' is chosen from $C_1$-$C_4$ alkyl radicals;

aminosulphonyl radicals (($R)_2N$—$SO_2$—) wherein the radicals R, which may be identical or different, are independently chosen from hydrogen and $C_1$-$C_4$ alkyl radicals;

alkylthio radicals (RS—) whererin the radical R is chosen from $C_1$-$C_4$ alkyl radicals; and alkylsulphonyl radicals (R—$SO_2$—) wherein the radical R is chosen from $C_1$-$C_4$ alkyl radicals.

In another embodiment of the present disclosure, the radicals $R_3$, which may be identical or different, may independently be chosen from:

$C_1$-$C_4$ alkyl radicals optionally substituted by at least one radical chosen from hydroxyl radicals, $C_1$-$C_2$ alkylcarbonylamino radicals, amino radicals substituted by two identical or different $C_1$-$C_2$ alkyl radicals which optionally carry at least one group chosen from hydroxyl groups and $C_1$-$C_2$ alkoxy radicals, it being possible for these two alkyl radicals optionally to form, with the nitrogen atom to which they are attached, a 5- or 6-membered heterocycle which is saturated or unsaturated and is optionally aromatic, for example chosen from pyrrolidine, piperazine, homopiperazine, pyrrole, imidazole and pyrazole;

$C_2$-$C_4$ hydroxyalkoxy radicals;

halogens, for example chlorine and fluorine;

amino radicals;

amino radicals substituted by one or two identical or different $C_1$-$C_2$ alkyl radicals which optionally carry at least one hydroxyl group;
methylcarbonylamino radicals;
methylsulphonylamino radicals;
hydroxyl radicals;
$C_1$-$C_2$ alkoxy radicals; and
methylsulphonyl radicals.

According to this embodiment of the present disclosure, the radicals $R_3$, which may be identical or different, may independently be chosen from:
a methyl, ethyl, propyl, 2-hydroxyethyl, methoxy, ethoxy, 2-hydroxyethyloxy, 3-hydroxypropyloxy and 2-methoxyethyl radicals;
methylsulphonylamino radicals;
amino, methylamino, dimethylamino and 2-hydroxyethylamino radicals;
methylcarbonylamino radicals;
hydroxyl radicals;
chlorine atoms; and
methylsulphonyl radicals.

According to a another embodiment of the present disclosure, when the coefficient m' is greater than or equal to 2, two adjacent radicals $R_3$ may form, with the carbon atoms to which they are attached, a secondary, 6-membered, aromatic ring optionally substituted by at least one group chosen from hydroxyl groups, $C_1$-$C_4$ alkyl radicals, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl-type radicals which optionally carry at least one hydroxyl group, —$NR_4$-Ph, —$NR_4$-Ph-$NR_5R_6$ and —$NR_4$-Ph-$OR_7$ radicals.

According to this embodiment of the present invention, two adjacent radicals $R_3$ may form, with the carbon atoms to which they are attached, a secondary, 6-membered, aromatic ring which is optionally substituted by at least one group chosen from hydroxyl groups, methoxy groups, ethoxy groups, 2-hydroxyethyloxy groups, amino groups, methylcarbonylamino groups, (di)-2-hydroxyethylamino groups, —NH-Ph groups, —NH-Ph-NH2 groups, —NH-Ph-NH-COCH3 groups, —NH-Ph-OH groups and —NH-Ph-OCH$_3$ groups.

With regard to the radicals $R_4$ and $R_7$, these radicals may be chosen from:
hydrogen;
$C_1$-$C_6$ alkyl radicals which are optionally substituted, for example by at least one group chosen from hydroxyl groups and $C_1$-$C_2$ alkoxy groups; and
aryl and arylalkyl radicals, such as phenyl or benzyl, the aryl moiety being optionally substituted, for example, by chlorine, amino groups, hydroxyl groups, $C_1$-$C_2$ alkoxy groups, amino groups which are mono- or disubstituted by two identical or different radicals chosen from $C_1$-$C_4$ alkyl radicals which optionally carry at least one hydroxyl group.

In accordance with one embodiment of the present disclosure, the radicals $R_4$ and $R_7$ may be chosen from:
hydrogen;
optionally substituted $C_1$-$C_3$ alkyl radicals, for example, methyl, ethyl, 2-hydroxyethyl and 2-methoxyethyl radicals; and
phenyl radicals which are optionally substituted by at least one radical chosen from hydroxyl radicals, $C_1$-$C_2$ alkoxy radicals, amino radicals, and amino radicals substituted by at least one $C_1$-$C_4$ group which optionally carry at least one hydroxyl group;

According to another embodiment, the radicals $R_4$ and $R_7$ are chosen from:
hydrogen;
methyl, ethyl and 2-hydroxyethyl radicals; and
phenyl radicals which are optionally substituted by at lease one radical chosen from hydroxyl, methoxy, amino, (di)methylamino and (di)(2-hydroxyethyl) amino radicals.

With regard to the radicals $R_5$ and $R_6$, independently of one another, these radicals are chosen from:
hydrogen;
alkylcarbonyl radicals (R—CO—) wherein R is chosen from optionally substituted $C_1$-$C_4$ alkyl radicals;
$C_1$-$C_6$ alkyl radicals which are optionally substituted by at least one identical or different group chosen from hydroxyl groups, $C_1$-$C_2$ alkoxy groups, amino groups and $C_1$-$C_4$ (di)alkylamino groups; the alkyl radical may further be substituted by at least one identical or different group chosen from $C_1$-$C_4$ alkylsulphonyl groups, $C_1$-$C_4$ alkylsulphinyl groups and $C_1$-$C_4$ alkylcarbonyl groups; and
aryl and arylalkyl radicals, for example, phenyl and benzyl radicals, the aryl moiety being optionally substituted by at least one identical or different group chosen from chlorine, amino groups, hydroxyl groups, $C_1$-$C_4$ alkoxy groups, and $C_1$-$C_4$ (di)alkylamino groups which optionally carry at least one hydroxyl group.

In accordance with one embodiment of the present disclosure, the radicals $R_5$ and $R_6$, which are identical or different, may be chosen from:
hydrogen;
methylcarbonyl, ethylcarbonyl and propylcarbonyl radicals;
optionally substituted $C_1$-$C_3$ alkyl radicals, for example, methyl, ethyl, 2-hydroxyethyl and 2-methoxyethyl radicals; and
phenyl radicals which are optionally substituted by at least one radical chosen from hydroxyl radicals, $C_1$-$C_2$ alkoxy radicals, amino radicals, and amino radicals substituted by at least one $C_1$-$C_4$ groups which optionally carry at least one hydroxyl group.

In another embodiment of the present disclosure, the radicals $R_5$ and $R_6$, which are identical or different, may be chosen from:
hydrogen;
methyl, ethyl and 2-hydroxyethyl radicals;
methylcarbonyl, ethylcarbonyl and propylcarbonyl radicals; and
phenyl radicals which are optionally substituted by at least one identical or different radical chosen from hydroxyl, methoxy, amino, (di)methylamino and (di) (2-hydroxyethyl)amino radicals.

According to one particular embodiment of the invention, the radicals $R_5$ and $R_6$ form, together with the nitrogen atom to which each is attached, a heterocycle comprising from 1 to 3 heteroatoms, for example, from 1 or 2 heteroatoms, chosen from N, O and S and comprising 5 to 7 ring members, which is saturated or unsaturated, aromatic or non-aromatic, and optionally substituted. In at least one embodiment, the heteroatom(s) may be nitrogen.

The heterocycle comprising 5 to 7 ring members may be chosen from the following heterocycles: piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, and 1-methyl-4-propylpyrrole.

In one embodiment of the present disclosure, the heterocycle comprising 5 to 7 ring members may be chosen from piperidine, piperazine, homopiperazine, pyrrole, imidazole and pyrazole heterocycles which are optionally substituted by at least one identical or different radical chosen from methyl, hydroxyl, amino and (di)methylamino radicals.

According to yet another embodiment of the present disclosure, the radicals $R_5$ and $R_6$ may be chosen from alkyl radicals which, independently of one another, form, with the carbon atom of the aromatic ring optionally substituted by at least one hydroxyl group, and adjacent to that to which —$NR_5R_6$ is attached, a 5- or 6-membered saturated heterocycle.

For example, the group —$NR_5R_6$ with the aromatic nucleus optionally substituted by a hydroxyl may correspond to the following compounds:

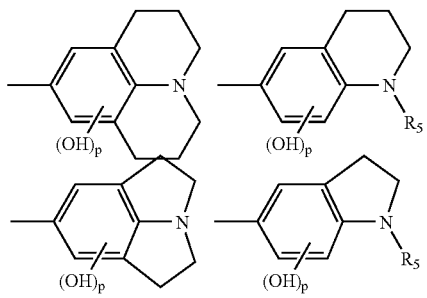

where p = 0 or 1

According to one embodiment, mention may be made of alkyl-type linkers L. Non-limiting examples of alkyl-type linkers L, may include methylene, ethylene, linear or branched propylene, linear or branched butylene, linear or branched pentylene, and linear or branched hexylene radicals which are optionally substituted and/or interrupted as indicated above.

These identical or different substituents may be chosen from hydroxyl, $C_1$-$C_2$ alkoxy, $C_1$-$C_2$ dialkylamino, ($C_1$-$C_4$ alkyl)carbonyl and $C_1$-$C_4$ alkyl sulphonyl substituents.

Non-limiting examples of aromatic or non-aromatic, saturated or unsaturated, cycles and heterocycles interrupting the alkyl radical of the linker L comprise phenylene, naphthylene, phenanthrylene, triazinyl, pyrimidinyl, pyridinyl, pyridazinyl, quinoxalinyl and cyclohexyl radicals.

Non-limiting examples of radicals L also comprise:

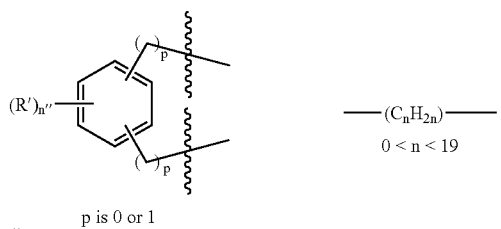

p is 0 or 1
n" is an integer between 0 and 4

—$(C_nH_{2n})$—
0 < n < 19

—$(C_nH_{2n})_2$—X
0 < n < 10
X = NH, NR$_4$, O
S, SO, SO$_2$

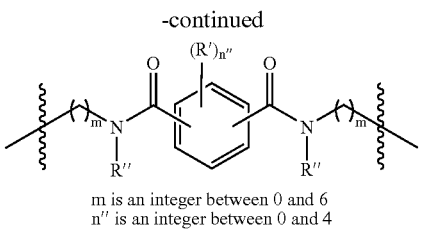

m is an integer between 0 and 6
n" is an integer between 0 and 4

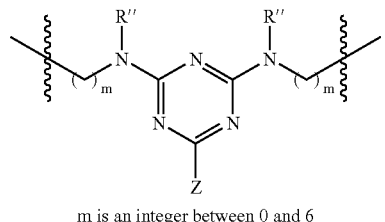

m is an integer between 0 and 6
Z = OH, NR$_8$R$_9$

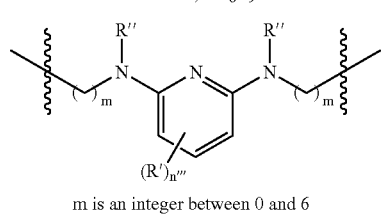

m is an integer between 0 and 6
n''' is an integer between 0 and 3

In these formulae:

R' has the same definition as $R_3$;

R" radicals, which are identical, are chosen from hydrogen and $C_1$-$C_4$ alkyl radicals;

$R_8$ and $R_9$, which may be identical or different are independently chosen from hydrogen and $C_1$-$C_8$ alkyl radicals which are optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino and optionally substituted phenyl radicals.

Non-limiting examples of the radicals L comprise:

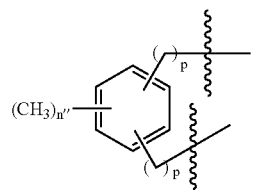

p is 0 or 1
n" is an integer between 0 and 4

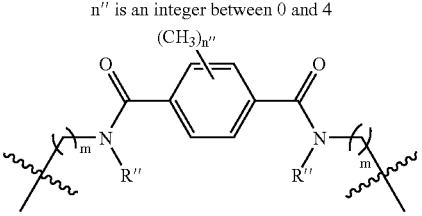

m is an integer between 0 and 6
n" is an integer between 0 and 4
The aromatic ring positions not substituted by a methyl radical carry a hydrogen atom In the formula (I) An is chosen an organic and inorganic anions and anion mixtures allowing the charge or charges on the compounds of formula (I) to be balanced. An may be chosen, for example, from halides such as chloride, bromide, fluoride and iodide; hydroxides; sulphates; hydrogensulphates; alkylsulphates for which the linear or branched alkyl moieties are chosen from $C_1$-$C_6$ radicals, such as the methylsulphate and ethylsulphate ions; carbonates and hydrogencarbonates; salts of carboxylic acids, such as formate, acetate, citrate, tartrate and oxalate; alkylsulphonates for which the linear or branched alkyl moieties are chosen from $C_1$-$C_6$ radicals, such as methylsulphonate ions; arylsulphonates for which the aryl moiety, for instance phenyl, is optionally substituted by at least one $C_1$-$C_4$ radical, such as 4-tolylsulphonate, for example; and alkylsulphonyls such as mesylate.

The acid addition salts of the compounds of formula (I) may be, by way of example, the addition salts with an organic or inorganic acid such as hydrochloric acid, hydrobromic acid, sulphuric acid and (alkyl- or phenyl-)sulphonic acids such as p-toluene-sulphonic acid and methylsulphonic acid.

The solvates of compounds of formula (I) include those chosen from hydrates of such compounds or the combination of at least one compound of formula (I) with at least one linear or branched $C_1$-$C_4$ alcohol such as methanol, ethanol, isopropanol and n-propanol.

In accordance with at least one embodiment of the compounds of the present disclosure may be chosen from compounds correspond to formula (I') below, and also to their resonance forms, their acid addition salts, and their solvates:

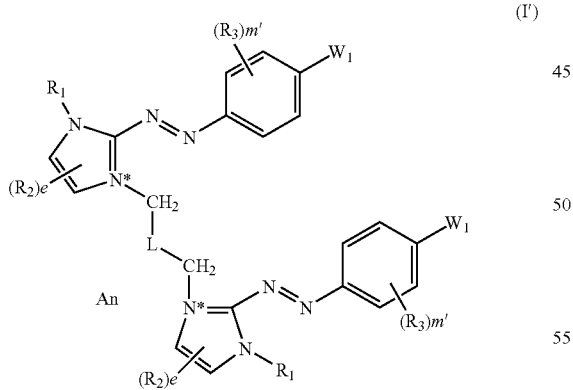
(I')

The $W_1$ groups, the radicals $R_1$, $R_2$ and $R_3$ and the coefficients e and m' being defined as above.

In accordance with one embodiment, compounds of the present disclosure may be chosen from compounds corresponding to one of the formulae below, and also to their resonance forms, their acid addition salts and their solvates:

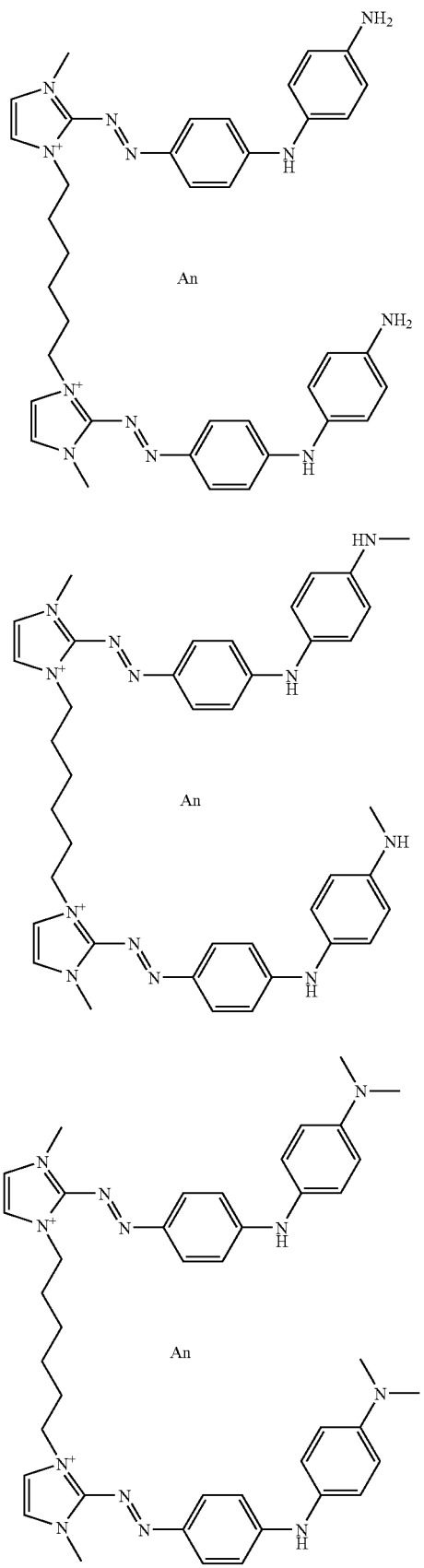

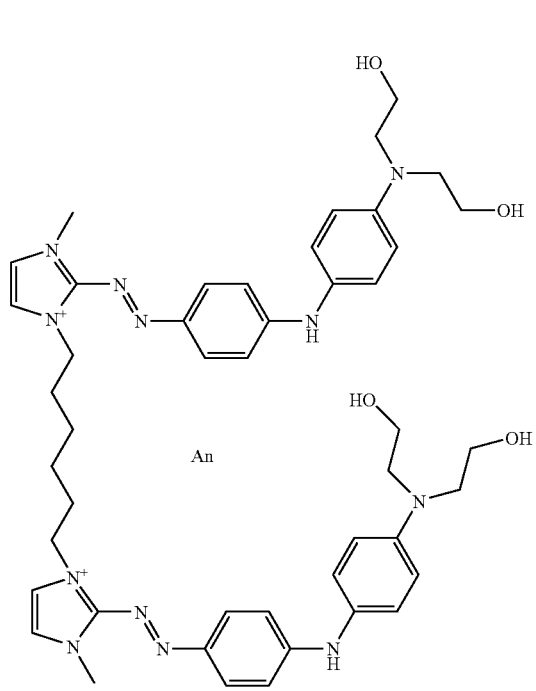
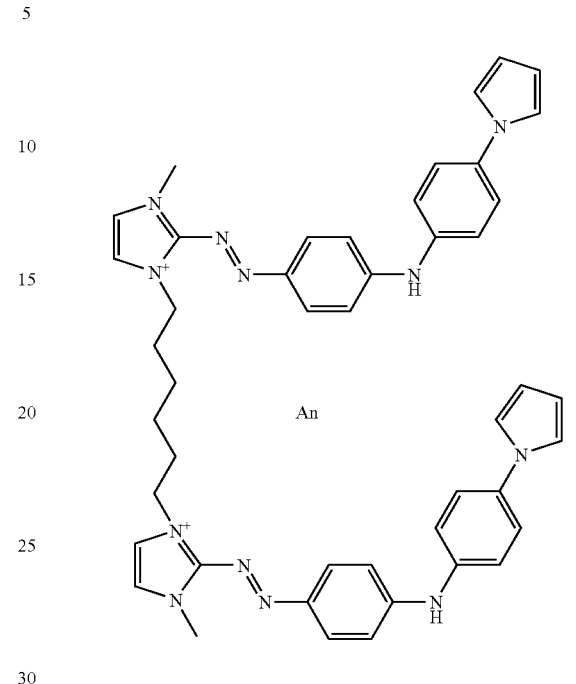
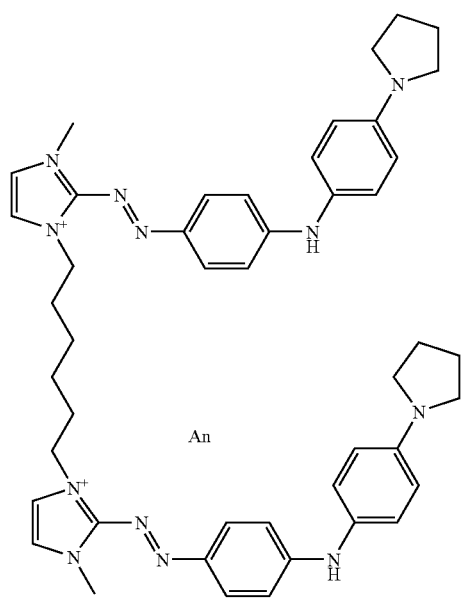
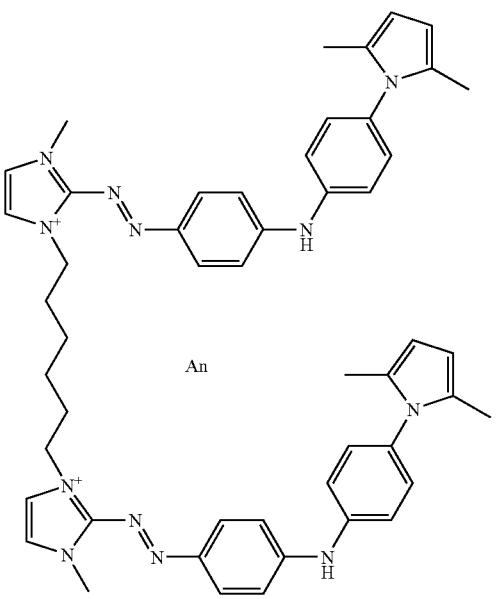

-continued
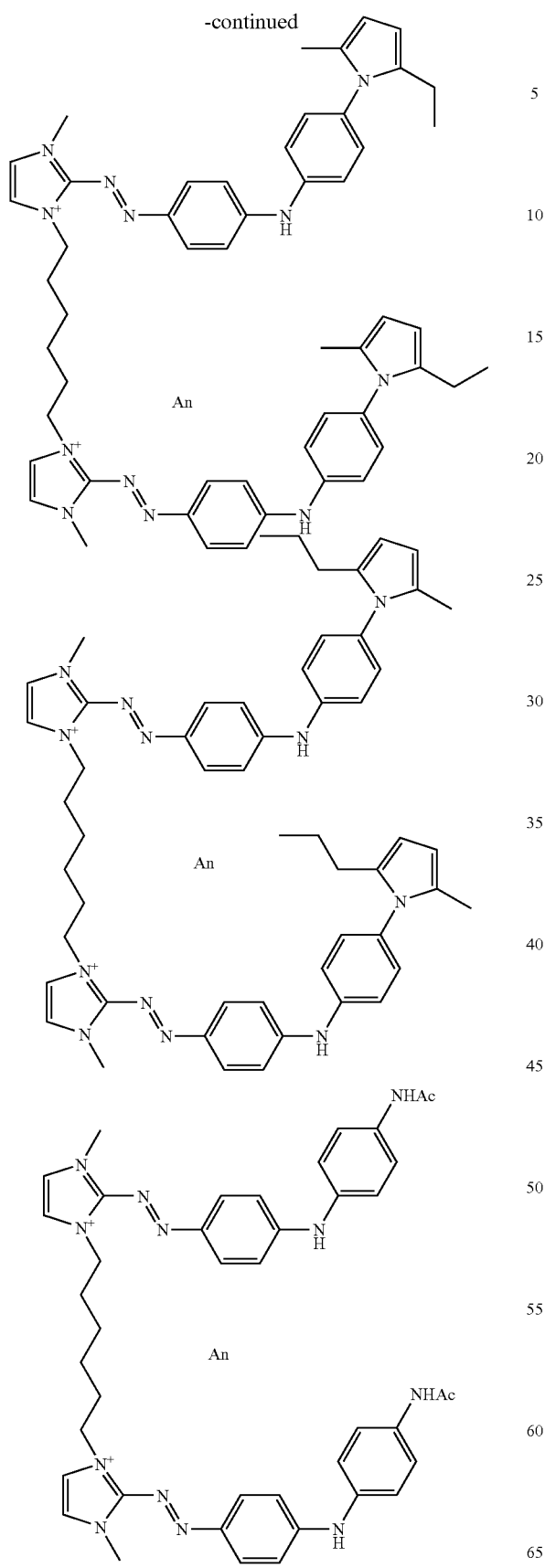
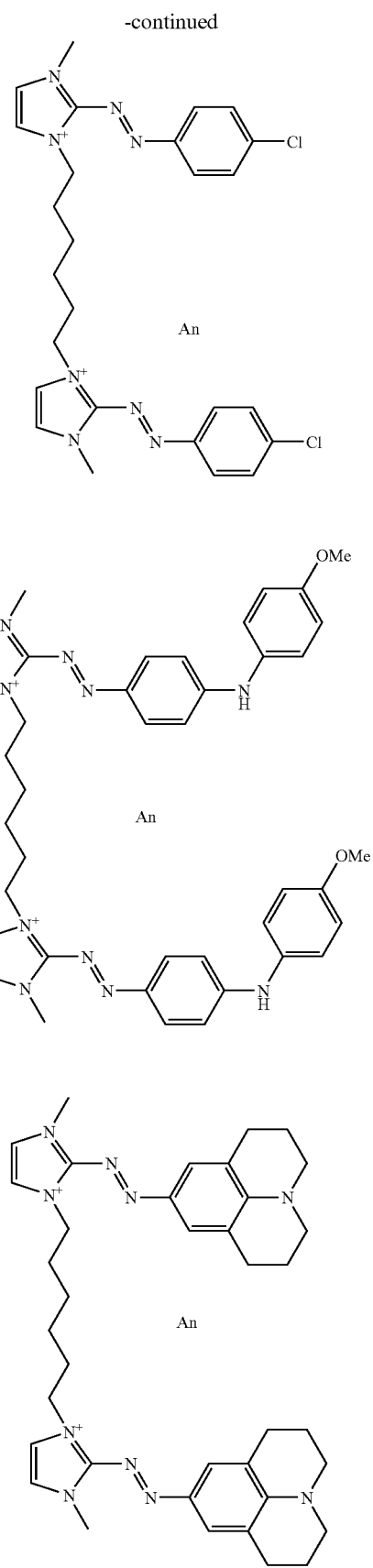

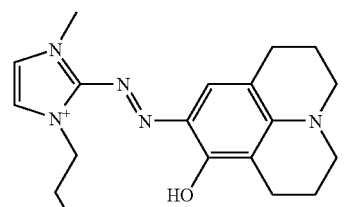
An
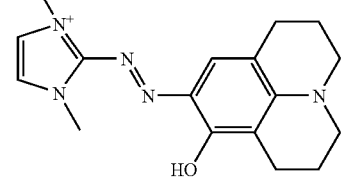
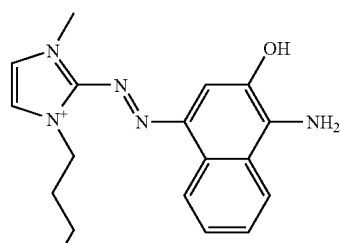
An
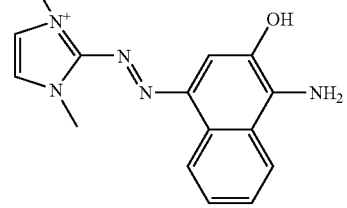
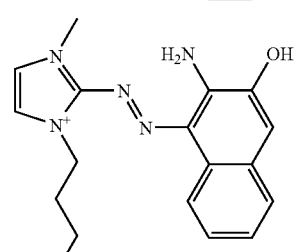
An
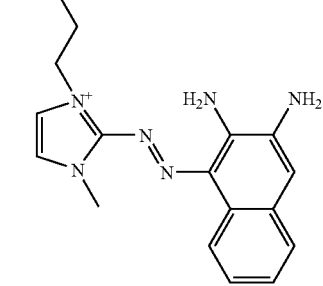
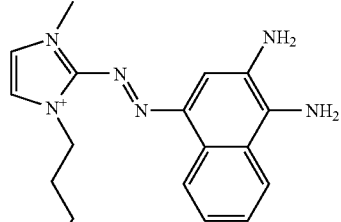
An
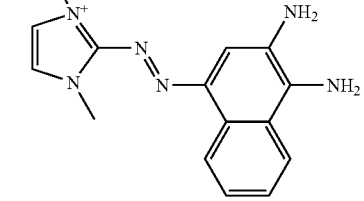
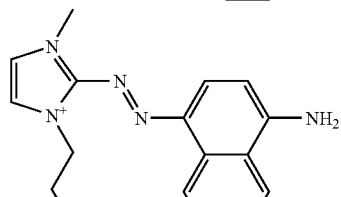
An
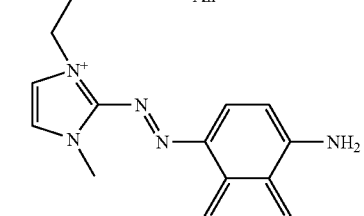
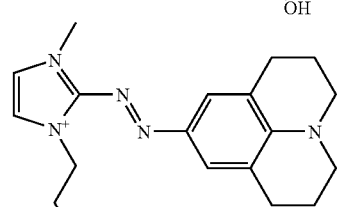
An
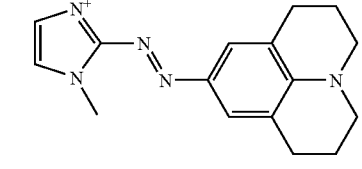

-continued
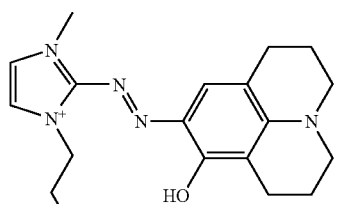
An
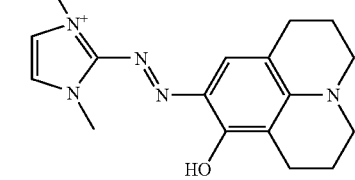
An
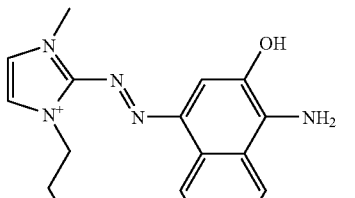
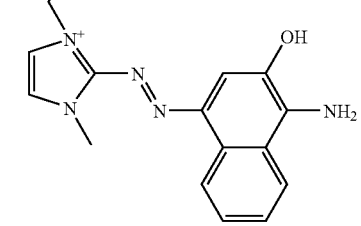
An
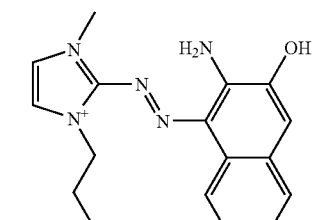
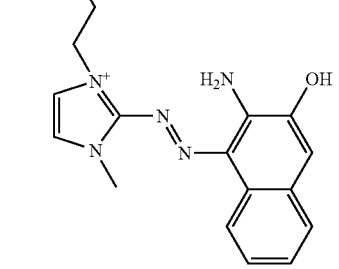
-continued
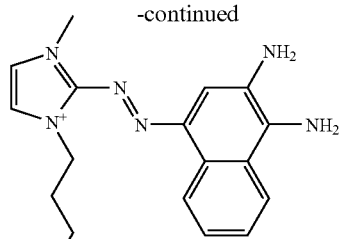
An
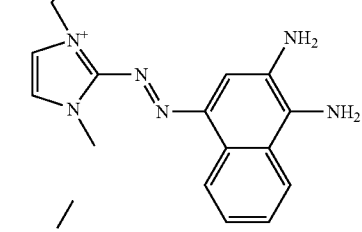
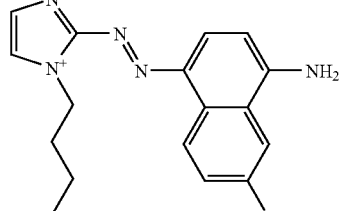
An
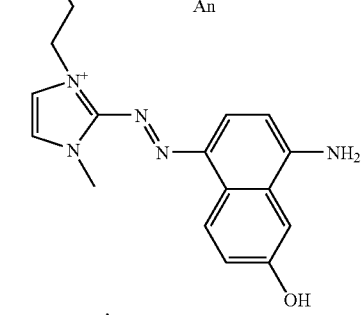
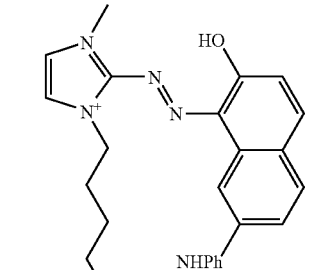
An
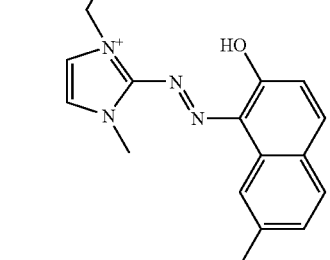

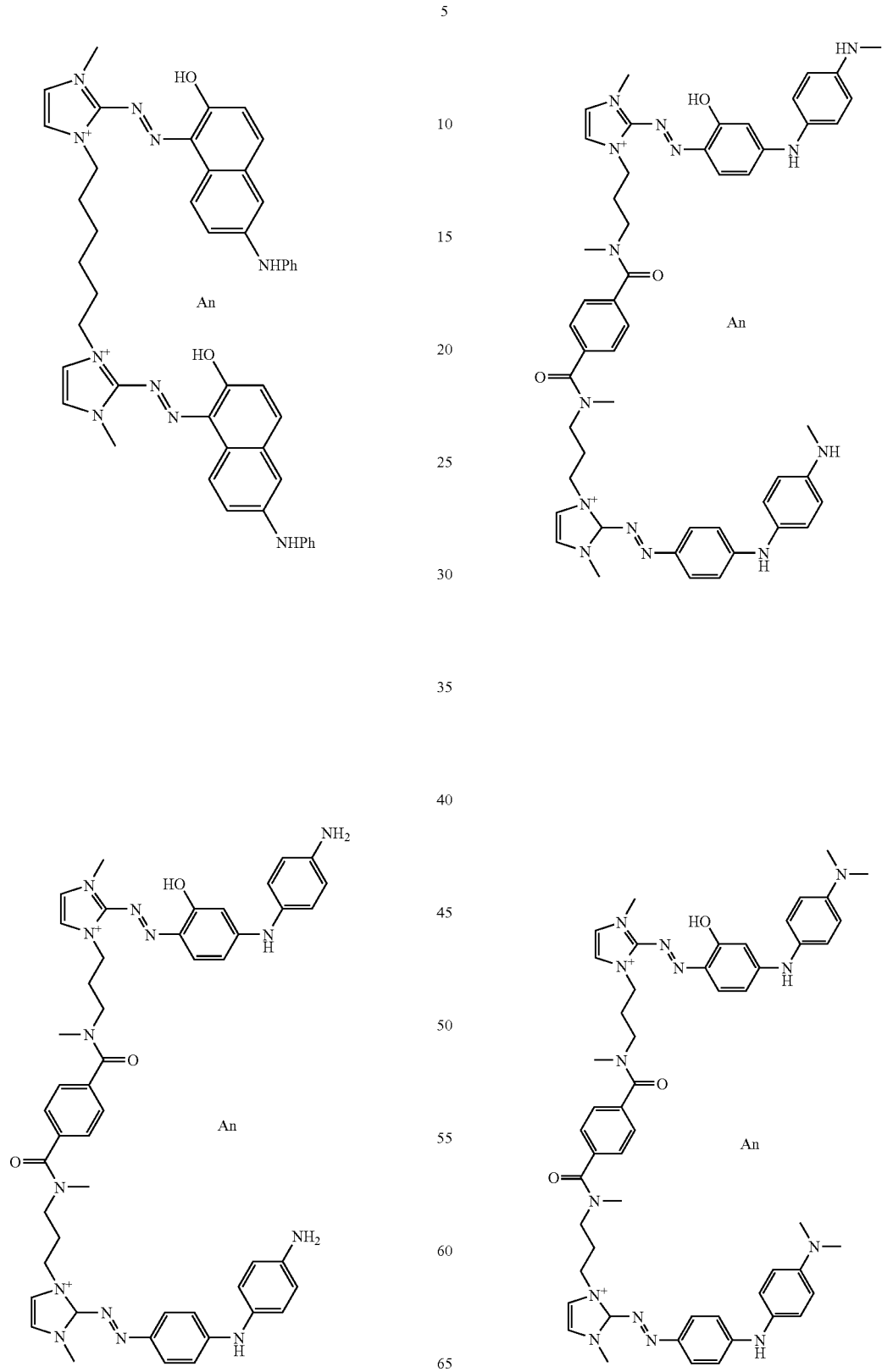

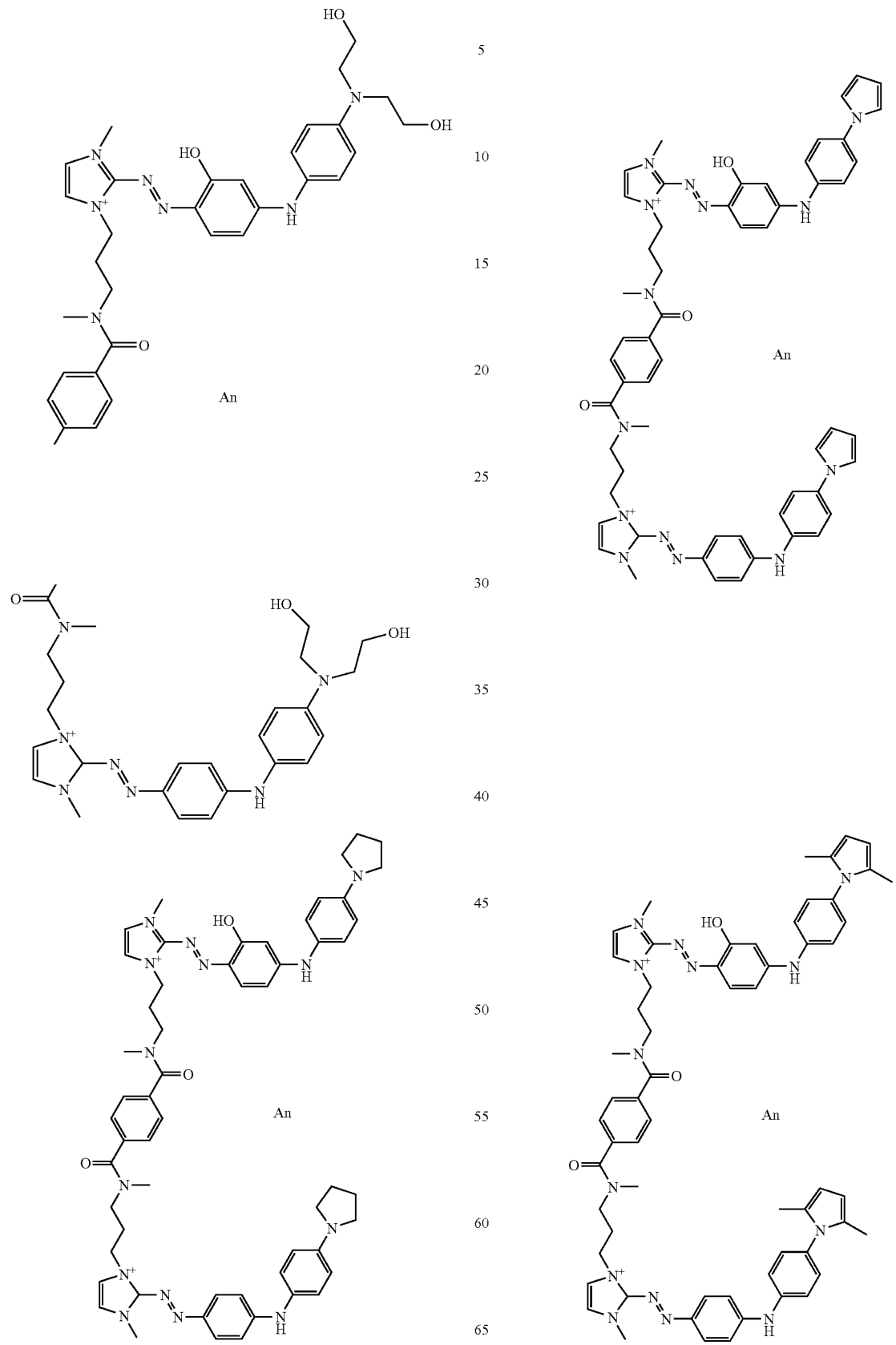

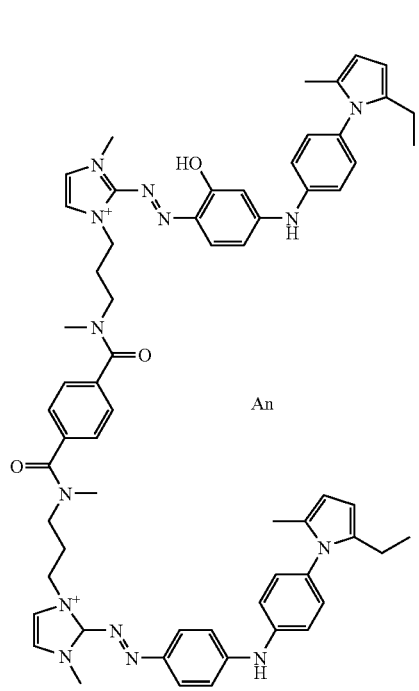
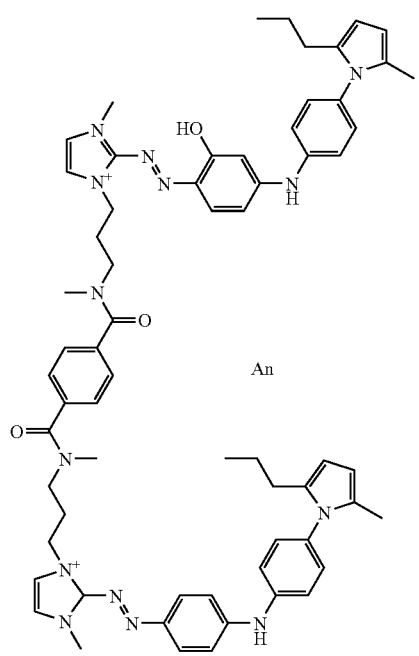
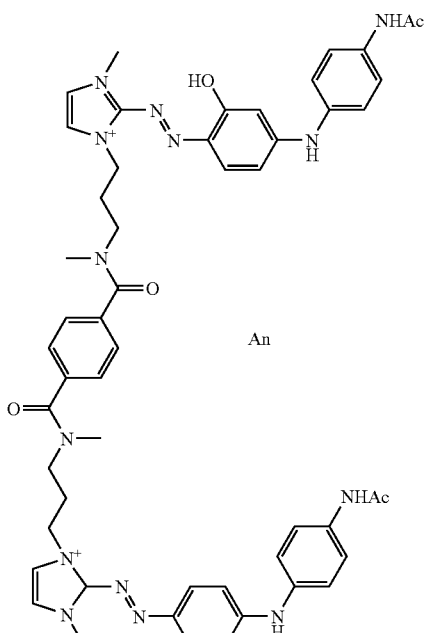
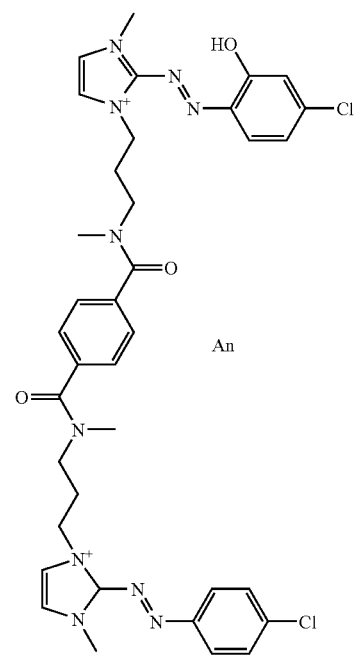

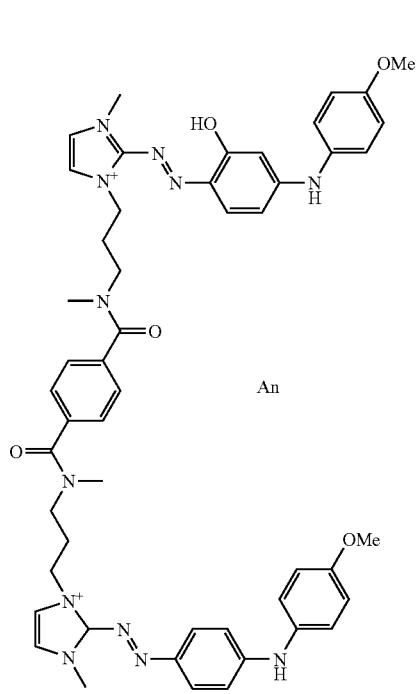
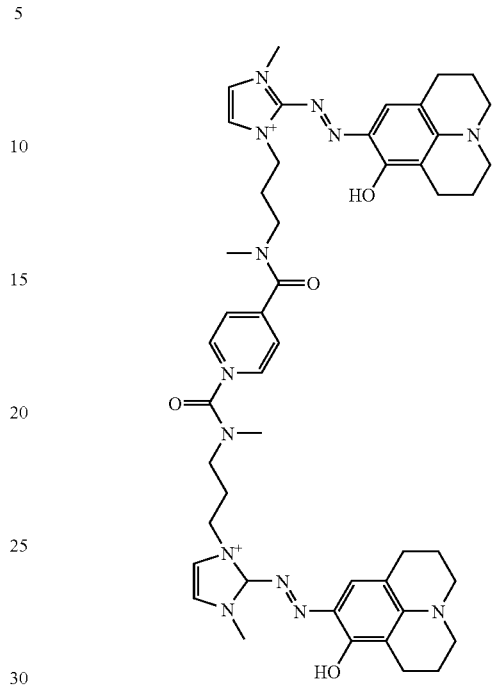
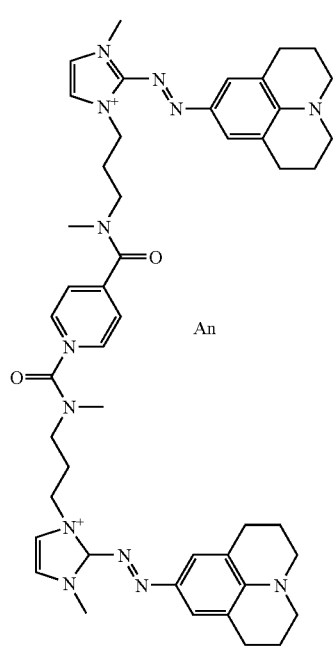
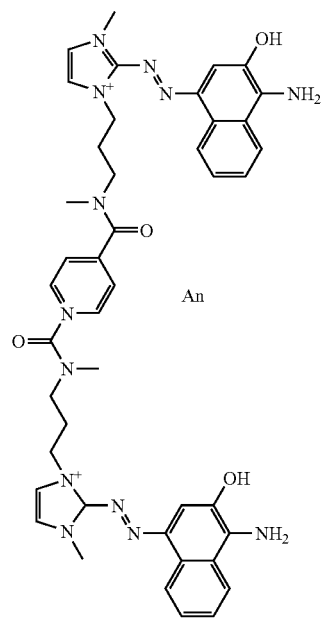

31
-continued
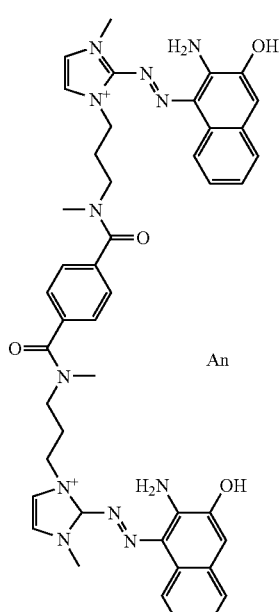
32
-continued
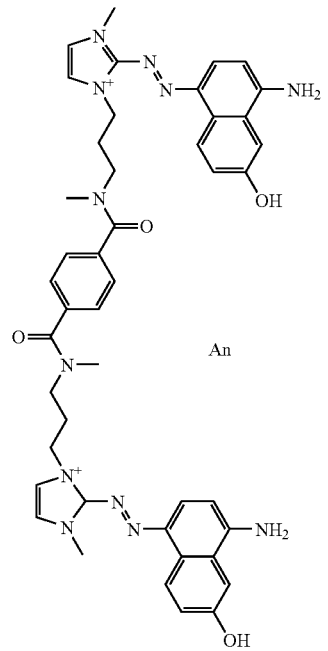
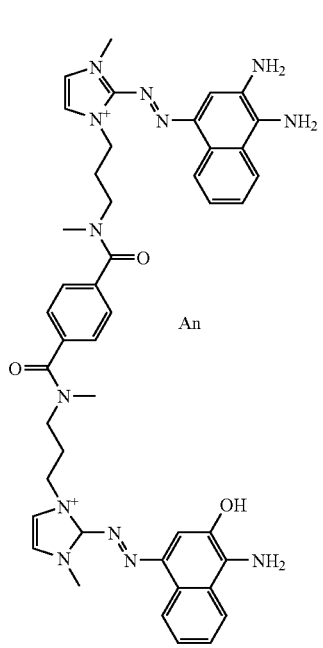
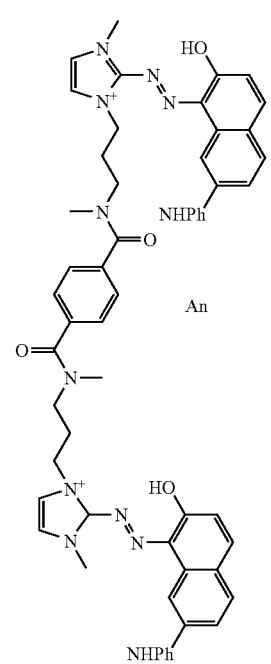

-continued

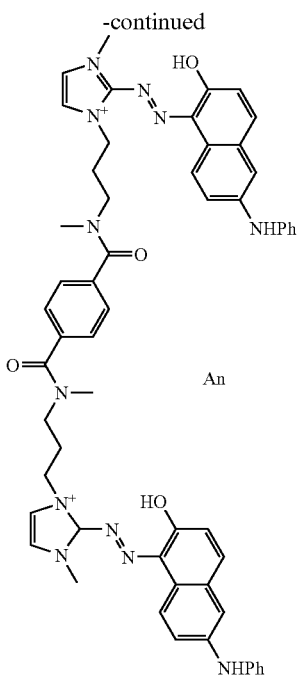

in which An is defined as before.

The compounds corresponding to the monoazo species may, for example, be obtained from preparation processes described, in U.S. Pat. No. 5,708,151, J. Chem. Res., Synop. (1998), (10), 648-9, U.S. Pat. No. 3,151,106, U.S. Pat. No. 5,852,179, Heterocycles, 1987, 26 (2) 313-7, Synth. Commun. 1999, 29 (13), 2271-6, Tetrahedron, 1983, 39 (7), 1091-1101. For preparation of the diazo compounds, reference may be made to European Patent Application No. 1377263 for a synthesis description.

The present disclosure further provides a dyeing composition comprising at least one of the compounds of formula (I), or its acid addition salt, as a direct dye in a medium appropriate for the dyeing of keratin fibers.

The at least one compound of formula (I) may be present in the dying composition in an amount ranging from 0.001% to 20% by weight relative to the total weight of the dyeing composition, for example, ranging from 0.01% to 10% by weight, such as ranging from 0.05% to 5% by weight.

According to the present disclosure, the dyeing composition may also comprise at lease one oxidation base. This oxidation base may be chosen from the oxidation bases conventionally used in oxidation dyeing, for example, para-phenylenediamines, bis(phenyl)alkylenediamines, para-aminophenols, ortho-aminophenols and heterocyclic bases.

Among the para-phenylenediamines that may be used, non-limiting mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

In one embodiment, suitable para-phenylenediamines may be chosen from, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof Further, among the bis(phenyl)alkylenediamines that may be used, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)-ethylenediamine, N,N'-bis(4-aminophenyl)tetramethylenediamine, N,N'-bis(α-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis (2,5-diaminophenoxy)-3,6-dioxaoctane, and the acid addition salts thereof.

Among the para-aminophenols that may be used, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Further, among the ortho-aminophenols that may be used, non-limiting mention may be made, for example, of 2-aminophenol, 2-amino-5-methylphenol, 2-amino-6-methylphenol and 5-acetamido-2-aminophenol, and the acid addition salts thereof.

Among the heterocyclic bases that may be used, non-limiting mention may be made, for example, of pyridine derivatives, pyrimidine derivatives and pyrazole derivatives.

Among the pyridine derivatives that may be used, non-limiting mention may be made of the compounds described, for example, in British Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Further, among the pyrimidine derivatives that may be used, non-limiting mention may be made of the compounds described, for example, in German Patent No. 2 359 399; Japanese Patent Nos. 88-169 571 and 05-163 124; European Patent No. 0 770 375 or World Patent Application No. 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent No. 2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-amino-pyrazolo[1,5-a]pyrimidin-7-yl) (2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Among the pyrazole derivatives that may be used, non-limiting mention may be made of the compounds described in German Patent Nos. 3 843 892 and 4 133 957 and World Patent Application Nos. 94/08969 and 94/08970, French Patent No. 2 733 749 and German Patent No. 195 43 988, such as, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-tri-aminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

According to the present disclosure, the dyeing composition may also comprise at least one coupler conventionally used for dyeing keratin fibers. Among these couplers, non-limiting mention may be made of meta-phenylenediamines, meta-aminophenols, meta-diphenols, naphthalenic couplers and heterocyclic couplers.

Non-limiting examples of the couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxy-ethylamino)toluene and the acid addition salts thereof.

In the dyeing composition of the present disclosure the oxidation base or bases may be present in an amount ranging from 0.001% to 10% by weight of the total weight of the dyeing composition, for example, ranging from 0.005% to 6% by weight.

The at least one coupler is generally present in a total amount ranging from 0.001% to 10% by weight of the total weight of the dyeing composition, for instance ranging from 0.005% to 6% by weight.

In general, the acid addition salts that may be used in the context of the dyeing compositions of the disclosure for the oxidation bases and couplers may be chosen, for example, from those listed in the context of the definition of the compounds of formula (I).

According to the present disclosure, the composition may optionally comprise at least one additional direct dye other than the compounds of formula (I). This dye may be chosen from cationic and nonionic species.

Non-limiting examples of the additional direct dye include nitrobenzene dyes, azo, azomethine, methine, tetraazapentamethine, anthraquinone, naphthoquinone, benzoquinone, phenothiazine, indigoid, xanthene, phenanthridine and phthalocyanine dyes, dyes derived from triarylmethane, natural dyes, and mixtures thereof.

The additional at least one direct dye may be chosen, for example, from the following red or orange nitrobenzene dyes:
  1-hydroxy-3-nitro-4-N-(γ-hydroxypropyl)aminobenzene,
  N-(β-hydroxyethyl)amino-3-nitro-4-aminobenzene,
  1-amino-3-methyl-4-N-(β-hydroxyethyl)amino-6-nitrobenzene,
  1-hydroxy-3-nitro-4-N-(β-hydroxyethyl)aminobenzene,
  1,4-diamino-2-nitrobenzene,
  1-amino-2-nitro-4-methylaminobenzene,
  N-(β-hydroxyethyl)-2-nitro-para-phenylenediamine,
  1-amino-2-nitro-4-(β-hydroxyethyl)amino-5-chlorobenzene,
  2-nitro-4-aminodiphenylamine,
  1-amino-3-nitro-6-hydroxybenzene,
  1-(β-aminoethyl)amino-2-nitro-4-(β-hydroxyethyloxy)benzene,
  1-(β,γ-dihydroxypropyl)oxy-3-nitro-4-(β-hydroxyethyl)aminobenzene,
  1-hydroxy-3-nitro-4-aminobenzene,
  1-hydroxy-2-amino-4,6-dinitrobenzene,
  1-methoxy-3-nitro-4-(β-hydroxyethyl)aminobenzene,
  2-nitro-4'-hydroxydiphenylamine, and
  1-amino-2-nitro-4-hydroxy-5-methylbenzene.

The at least one additional direct dye may also be chosen from the following yellow and green-yellow nitrobenzene direct dyes:
  1-β-hydroxyethyloxy-3-methylamino-4-nitrobenzene,
  1-methylamino-2-nitro-5-(β,γ-dihydroxypropyl)oxybenzene,
  1-(β-hydroxyethyl)amino-2-methoxy-4-nitrobenzene,
  1-(β-aminoethyl)amino-2-nitro-5-methoxybenzene,
  1,3-di(β-hydroxyethyl)amino-4-nitro-6-chlorobenzene,
  1-amino-2-nitro-6-methylbenzene,
  1-(β-hydroxyethyl)amino-2-hydroxy-4-nitrobenzene,
  N-(β-hydroxyethyl)-2-nitro-4-trifluoromethylaniline,
  4-(β-hydroxyethyl)amino-3-nitrobenzenesulphonic acid,
  4-ethylamino-3-nitrobenzoic acid,
  4-(β-hydroxyethyl)amino-3-nitrochlorobenzene,
  4-(β-hydroxyethyl)amino-3-nitromethylbenzene,
  4-(β,γ-dihydroxypropyl)amino-3-nitrotrifluoromethylbenzene,
  1-(β-ureidoethyl)amino-4-nitrobenzene,
  1,3-diamino-4-nitrobenzene,
  1-hydroxy-2-amino-5-nitrobenzene, 1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

The at least one additional direct dye may also be chosen from the following blue or violet nitrobenzene direct dyes:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

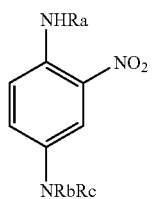

wherein:
Rb is chosen from $C_1$-$C_4$ alkyl radicals, β-hydroxyethyl groups, β-hydroxypropyl groups, and γ-hydroxypropyl radicals;
Ra and Rc, which may be identical or different, are independently chosen from β-hydroxyethyl, β-hydroxypropyl, γ-hydroxypropyl and β,γ-dihydroxypropyl radicals, at least one of the radicals Rb, Rc or Ra are chosen from y-hydroxypropyl radicals and Rb and Rc not being able to denote simultaneously a β-hydroxyethyl radical when Rb is a γ-hydroxypropyl radical, such as those described in French Patent No. 2 692 572.

Among the azo direct dyes that may be used according to the present disclosure, non-limiting mention may be made of the cationic azo dyes described in International Patent Applications Nos. 95/15144, and 95/01772, European Patent No. 714954, French Patent Nos. 2 822 696, 2 825 702, 2 825 625, 2 822 698, 2 822 693, 2 822 694, 2 829 926, and 2 807 650, International Patent Application Nos. 02/078660, 02/100834, and 02/100369, and French Patent No. 2 844 269.

Among these compounds, non-limiting mention may be made of the following dyes:
1,3-dimethyl-2[[4-dimethylamino)phenyl]azo]1H-imidazolium chloride,
1,3-dimethyl-2-[(4-aminophenyl)azo]-1H-imidazolium chloride,
1-methyl-4-[(methylphenylhydrazono)methyl]pyridinium methylsulphate.

Non-limiting mention may be made of the following azo direct dyes described in the Color Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24, and
Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Non-limiting mention may also be made of the following quinone direct dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also non-limiting mention may also be made of the following compounds:
1-N-methylmorpholiniumpropylamino-4-hydroxyanthraquinone
1-aminopropylamino-4-methylaminoanthra-quinone
1-aminopropylaminoanthraquinone
5-β-hydroxyethyl-1,4-diaminoanthraquinone
2-aminoethylaminoanthraquinone, and
1,4-bis(β,γ-dihydroxypropylamino)anthraquinone.

Further, non-limiting mention may also be made of the following azine dyes:
Basic Blue 17, and
Basic Red 2.

Non-limiting mention may be made of the following triarylmethane dyes that may be used according to the present disclosure:
Basic Green 1
Acid Blue 9
Basic Violet 3
Basic Violet 14
Basic Blue 7
Acid Violet 49
Basic Blue 26, and
Acid Blue 7.

Among the indoamine dyes that may be used according to the present disclosure, non-limiting mention may be made of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetyl-amino-6-methoxy-1,4-benzoquinoneimine;
3-N-(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Among the dyes of tetraazapentamethine type that may be used according to the present disclosure, non-limiting mention may be made of the following compounds given in the table below, An being defined as above:

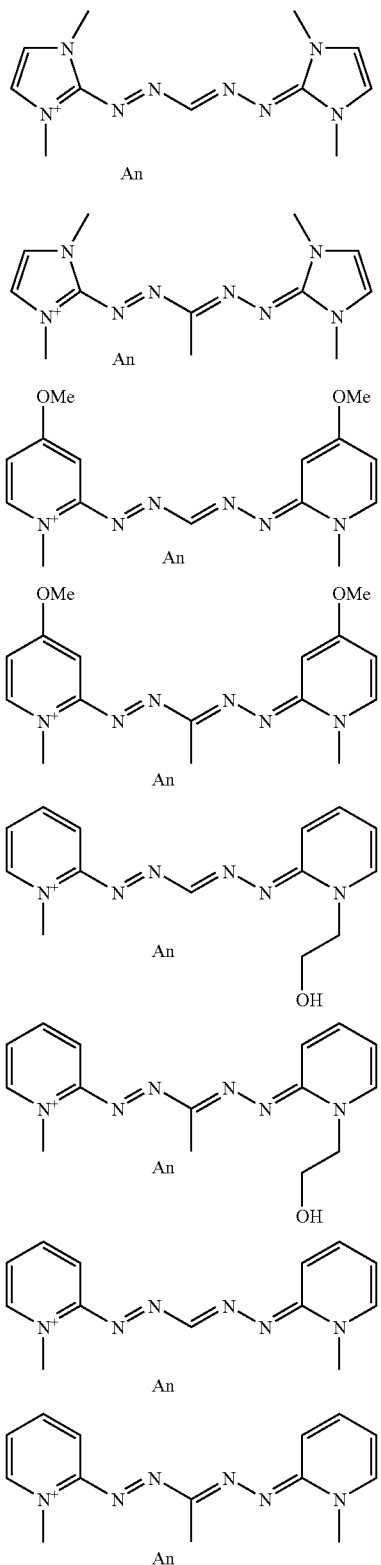

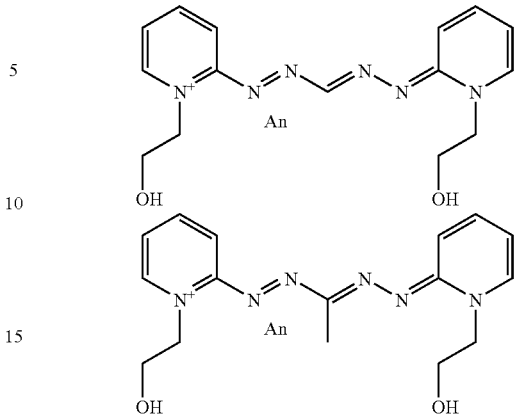

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Extracts or decoctions comprising these natural dyes may also be used, and for example henna-based poultices or extracts.

When they are present, the at least one additional direct dye is present in the composition in an amount ranging from 0.001% to 20% by weight relative to the weight of the composition and, for example, ranging from 0.01% to 10% by weight relative to the weight of the composition.

The medium that is suitable for dyeing, also known as the dye vehicle, generally comprises water or a mixture of water and at least one organic solvent to dissolve any compounds that would not be sufficiently water-soluble.

The organic solvents may be chosen from linear or branched, for example, saturated or unsaturated monoalcohols and diols comprising 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for example, ethylene glycol monomethyl, monoethyl and monobutyl ether, propylene glycol and its ethers, for example, propylene glycol monomethyl ether, butylene glycol and dipropylene glycol; and also diethylene glycol alkyl ethers, such as the $C_1$-$C_4$ ethers, for example, diethylene glycol monoethyl ether, monobutyl ether, and mixtures thereof.

The at lease on organic solvent may be present in the dying composition in an amount ranging from 1% to 40% by weight and, for example, from 5% to 30% by weight, relative to the total weight of the composition.

The dyeing composition in accordance with the present disclosure may also comprise at least one adjuvant conventionally used in compositions for dyeing keratin fibers such as the hair, for example, anionic, cationic, nonionic, amphoteric and zwitterionic surfactants or mixtures thereof; anionic, cationic, nonionic, amphoteric and zwitterionic polymers or mixtures thereof; mineral or organic thickeners, and for example, anionic, cationic, nonionic and amphoteric polymeric associative thickeners; antioxidants; penetrants; sequestrants; fragrances; buffers; dispersants; conditioning agents, for example silicones, which may or may not be volatile or be modified; film-forming agents; ceramides; preservatives; and opacifiers.

The least one adjuvant above are generally present in an amount for each of them ranging from 0.01% to 20% by weight relative to the weight of the composition.

The person skilled in the art will of course take care to choose this at least one optional additional compound such that the advantageous properties intrinsically associated with the oxidation dyeing composition in accordance with the present disclosure are not, or not substantially, adversely affected by the envisaged addition.

According to one embodiment of the present disclosure, the pH of the dyeing composition ranges from 3 to 12, for example, ranging from 5 to 11. The pH may be adjusted to the desired value using acidifying or alkalifying agents usually used in the dyeing of keratin fibers, or alternatively using standard buffer systems.

Non-limiting mention may be made of the following suitable acidifying agents: mineral or organic acids, for example hydrochloric acid; orthophosphoric acid; sulphuric acid; carboxylic acids, such as, acetic acid, tartaric acid, citric acid and lactic acid; and sulphonic acids.

Further, non-limiting mention may be made of the following suitable alkalifying agents: aqueous ammonia, alkaline carbonates, alkanolamines for example monoethanolamine, diethanolamine and triethanolamine and derivatives thereof, sodium hydroxide, potassium hydroxide and the compounds having the following formula:

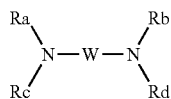

wherein W is a propylene residue optionally substituted by at least one group chosen from hydroxyl groups and $C_1$-$C_4$ alkyl radicals; Ra, Rb, Rc and Rd, which are identical or different, are chosen from hydrogen $C_1$-$C_4$ alkyl radicals, and $C_1$-$C_4$ hydroxyalkyl radicals.

The dyeing composition according to the present disclosure may be in various forms, such as in the form of liquids, creams or gels, or in any other form that is suitable for dyeing keratin fibers, such as human hair.

The composition according to the present disclosure may further comprise at least one oxidizing agent. In this case, the composition may be referred to as a ready-to-use composition.

For the purposes of the present disclosure, a ready-to-use composition is a composition intended to be applied immediately to the keratin fibers, i.e. it may be stored in unmodified form before use or may result from the extemporaneous mixing of two or more compositions.

The ready-to-use composition may also be obtained by mixing the composition according to the present disclosure with an oxidizing composition.

The at least one oxidizing agent may be any oxidizing agent conventionally used in the field. Thus, for example, it may be chosen from hydrogen peroxide, urea peroxide, alkali metal bromates, persalts such as perborates and persulphates, and also enzymes, among which non-limiting mention may be made of peroxidases, 2-electron oxidoreductases such as uricases, and 4-electron oxygenases, for instance laccases. In at least one embodiment, the at least one oxidizing agent is hydrogen peroxide.

The at least one oxidizing agent may be present in an amount ranging from 1% to 40% by weight, relative to the weight of the ready-to-use composition, and, for example, ranging from 1% to 20% by weight relative to the weight of the ready-to-use composition.

In at least one embodiment, the oxidizing composition used is an aqueous composition and may be in the form of a solution or an emulsion.

According to one embodiment of the present disclosure, the composition free of oxidizing agent is mixed with 0.5 to 10 weight equivalents of the oxidizing composition.

It should be noted that the pH of the ready-to-use composition may range from 4 to 12, for example from 7 to 11.5.

The pH of the composition may be adjusted using an acidifying or alkalifying agent chosen from those mentioned previously in the context of the description according to the present disclosure.

The present disclosure further provides a method of coloring that comprises the application of a dyeing composition according to the present disclosure to the wet or dry keratin fibers.

The application to the fibers of the dyeing composition comprising at least one compound of formula (I) or the acid addition salts thereof, optionally at least one oxidation base optionally combined with at least one coupler, and optionally at least one additional direct dye, may be performed in the presence of at least one oxidizing agent.

The at least one oxidizing agent may be added to the composition comprising the at least one compound of formula (I) and the optional oxidation bases, couplers and/or additional direct dyes, either at the time of use or directly on the keratin fiber.

The oxidizing composition may also include various adjuvants conventionally used in compositions for dyeing the hair and as defined above.

The pH of the oxidizing composition comprising the at least one oxidizing agent is such that, after mixing with the dye composition, the pH of the resulting composition applied to the keratin fibers ranges from 4 to 12, for example, from 7 to 11.5. It may be adjusted to the desired value by means of acidifying or alkalifying agents usually used in the dyeing of keratin fibers and as defined above.

The composition that finally contacts the keratin fibers may be in various forms, chosen from, for example, liquids, creams and gels or in any other form that is suitable for dyeing keratin fibers, such as human hair.

According to one particular embodiment of the present disclosure, the dyeing composition according to the disclosure may be free of oxidation base and of coupler.

In another embodiment, the composition applied may optionally comprise at least one oxidizing agent.

The composition is thus contacted with the wet or dry keratin fibers and is then left in contact with the fibers for a leave-in time that is sufficient to give the desired coloration.

Whether the dyeing composition does or does not comprise an oxidizing agent, the leave-in time generally ranges from a few seconds to one hour, for instance ranging from 3 to 30 minutes.

The temperature at which the composition is left to act generally ranges from 15 to 220° C., for example, ranging from 15 to 80° C., such as from 15 to 40° C.

After the leave-in time, the composition may be removed by rinsing with water, optionally followed by washing with a shampoo, and then optionally by drying.

Another aspect of the present disclosure is a device having a plurality of compartments or a dyeing kit, wherein a first compartment comprises a dyeing composition of the present disclosure and a second compartment comprises at least one oxidizing composition. This device may be equipped with a means for delivering the desired mixture to the hair, such as the devices described in French Patent No. 2 586 913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the invention in a non-limiting manner.

EXAMPLES

1-Synthesis of Compounds

Synthesis of Compound 2

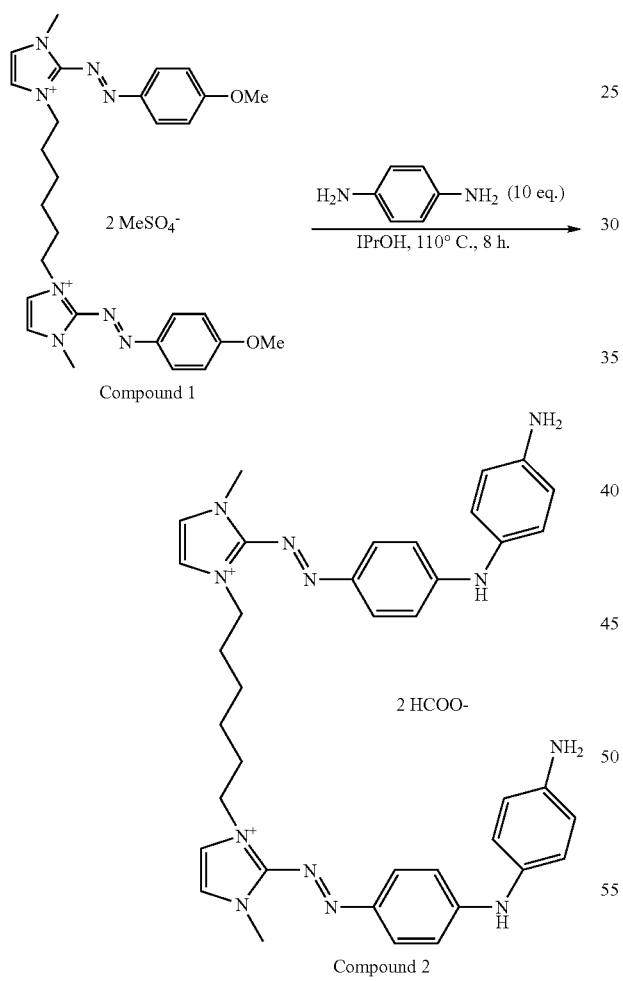

Synthesis of Compound 5

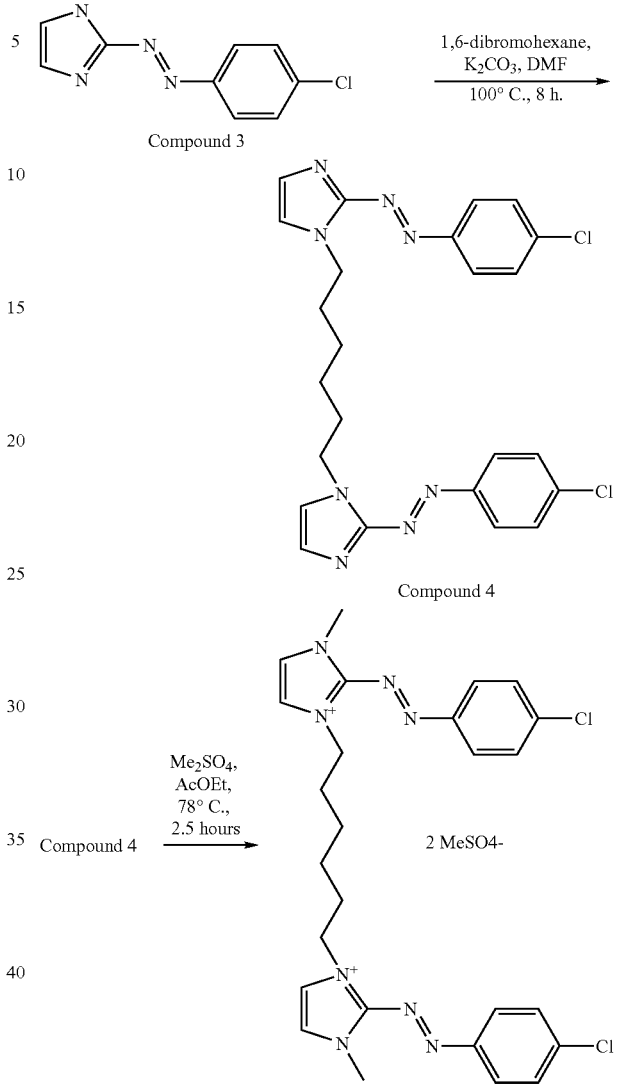

Compound 1 (1.477 g, n=0.002 mol) was reacted in the presence of 1.08 g (n=0.02 mol) of p-phenylenediamine in 20 ml of isopropanol at 100° C. for 8 hours. Concentration of the reaction mixture gave a violet residue. Purification by liquid chromatography was required and gave the pure compound 2 in the form of a violet-colored powder.

The $^1$H NMR and mass analyses were in accordance with the expected product.

Compound 3 was obtained by reacting the diazonium salt of p-chloroaniline in the presence of imidazole.

Step 1:

Compound 3 (2.03 g) was reacted in the presence of 0.78 ml of 1,6-dibromohexane and 0.69 g of potassium carbonate in 30 ml of dimethylformamide at 100° C. for 8 hours. The reaction mixture was brought to ambient temperature. A red precipitate was obtained by precipitation from ethyl acetate. Filtration under vacuum, washing with ethyl acetate and drying in a desiccator under vacuum gave 2.3 g of a red powder (compound 4).

The $^1$H NMR and mass analyses were in accordance with the expected product.

Step 2:

Compound 4 (3.2 g) was reacted in the presence of 3 ml of dimethyl sulphate in 30 ml of ethyl acetate at 78° C. for 2.5 hours. The reaction mixture was brought to ambient temperature. A red precipitate was formed. Filtration under vacuum, washing with ethyl acetate and drying in a desiccator under vacuum gave 4 g of a red powder (compound 5).

The $^1$H NMR and mass analyses were in accordance with the expected product.

2 Coloring Under Non-Oxidizing Conditions $5 \times 10^{-4}$ mol of compound 2 obtained above was dissolved in 5 ml of a mixture of water (2.5 ml) and pH 10 buffer (2.5 ml) of the following composition:

2 g of ammonium acetate 40 ml of water

NH$_3$ at 20% to pH 9-10 water to 100 ml 100 g of the above composition was applied to hair at ambient temperature for 30 minutes. The hair was subsequently rinsed, optionally washed, and dried.

The hair was colored violet.

$5 \times 10^{-4}$ mol of compound 5 obtained above was dissolved in 5 ml of a mixture of water (2.5 ml) and pH 10 buffer (2.5 ml) of the following composition:

2 g of ammonium acetate 40 ml of water

NH$_3$ at 20% to pH 9-10 water to 100 ml 100 g of the above composition was applied to hair at ambient temperature for 30 minutes. The hair was subsequently rinsed, optionally washed, and dried.

The hair was colored orange-yellow.

Comparative Results

Color After Shampooing of Dyes 2 and 6

After 6 shampooings at 2% the tress of dye 6 lost coverage and gloss, in contrast to the tress of dye 2.

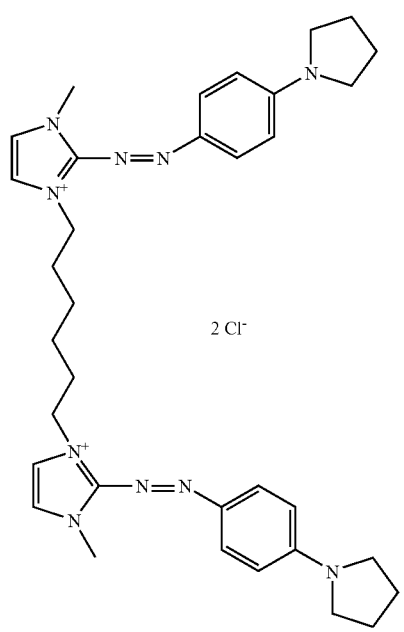

Dye 6

Light-Induced Color Change of Dyes 5 and 7

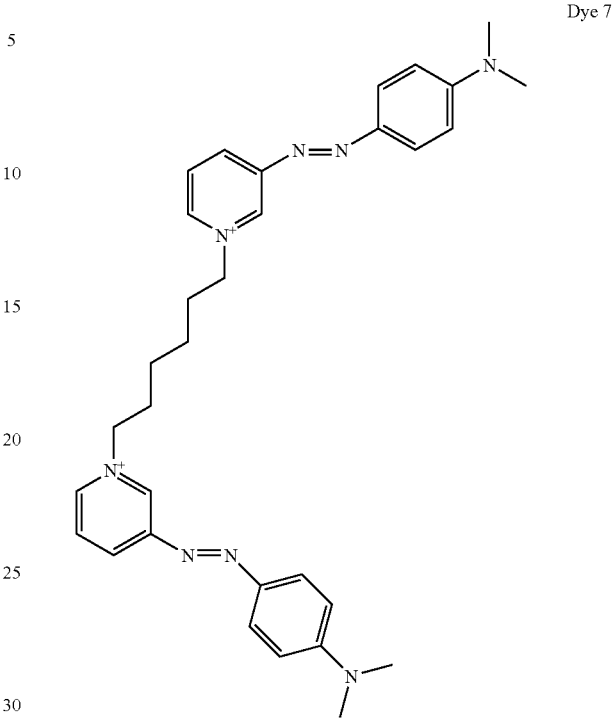

Dye 7

The light-induced degradation studies demonstrated that the dyes can undergo degradation in light to a greater or lesser extent. This light-induced degradation may lead in certain cases to an attenuation, or even to the disappearance, of the color on hair. Studies have shown that dye 7, in contrast to dye 5, led to a very great attenuation of the color following light exposure.

What is claimed is:

1. A symmetrical cationic diazo compound chosen from those of formula (I) below, their resonance forms, and their acid addition salts and their solvates:

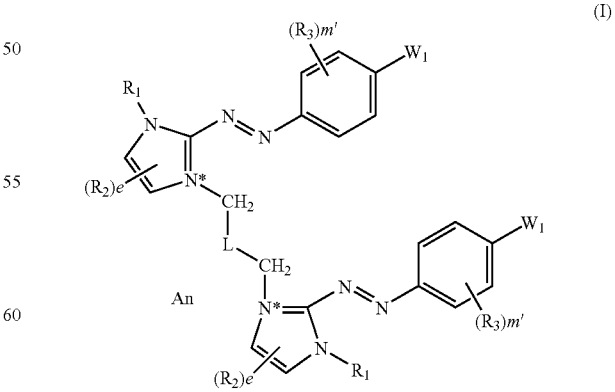

wherein:

the radicals $R_1$, which are identical or not, are chosen from:
optionally substituted $C_1$-$C_4$ alkyl radicals;

optionally substituted phenyl radicals; and
optionally substituted benzyl radicals;

the radicals $R_2$, which may be identical or different, are chosen from:

optionally substituted $C_1$-$C_{16}$ alkyl radicals optionally interrupted by at least one entity chosen from heteroatom and groups comprising at least one heteroatom, the alkyl radical being further optionally substituted by at least one group chosen from thio (—SH), $C_1$-$C_4$ thioalkyl; $C_1$-$C_4$ alkylsulphinyl or $C_1$-$C_4$ alkylsulphonyl groups;

hydroxyl groups, $C_1$-$C_4$ alkoxy groups, $C_2$-$C_4$ (poly)hydroxyalkoxy groups;

alkoxycarbonyl groups (RO—CO—) wherein R is chosen from $C_1$-$C_4$ alkyl radicals, alkylcarbonyloxy radicals (RCO—O—) wherein R is chosen from $C_1$-$C_4$ alkyl radicals, alkylcarbonyl radicals (R—CO—) wherein R is chosen from $C_1$-$C_4$ alkyl radicals, amino groups, amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O and S and 5 to 7 ring members, which is saturated or unsaturated, aromatic or non-aromatic and optionally substituted;

alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;

aminocarbonyl groups ((R)$_2$N—CO—) wherein the radicals R independently of one another are chosen from hydrogen and $C_1$-$C_4$ alkyl radicals;

ureido groups (N(R)$_2$—CO—NR'—) wherein the radicals R and R' independently of one another are chosen from hydrogen and $C_1$-$C_4$ alkyl radicals;

aminosulphonyl groups ((R)$_2$N—SO$_2$—) wherein the radicals R independently of one another are chosen from hydrogen and $C_1$-$C_4$ alkyl radicals;

alkylsulphonylamino groups (RSO$_2$—NR'—) wherein R is chosen from $C_1$-$C_4$ alkyl radicals and R' is chosen from hydrogen and $C_1$-$C_4$ alkyl radicals;

optionally substituted aryl radicals;

optionally substituted ($C_1$-$C_4$) alkylaryl radicals;

alkylsulphinyl groups (R—SO—) wherein R is chosen from $C_1$-$C_4$ alkyl radicals;

alkylsulphonyl groups (R—SO$_2$—) wherein R is chosen from $C_1$-$C_4$ alkyl radicals;

nitro groups;

cyano groups;

halogen atoms;

thio groups (HS—); and alkylthio groups (RS—) wherein the radical R is chosen from optionally substituted $C_1$-$C_4$ alkyl radicals;

when e is 2, the two radicals $R_2$ may optionally form, with the carbon atoms to which they are attached, a secondary ring, aromatic or non-aromatic, comprising 5 or 6 ring members which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

e is an integer from 0 to 2; when e is less than 2, one or more unsubstituted carbon atom(s) of the heterocycle carry a hydrogen atom, the radicals $R_3$, which may be identical or different, are chosen from:

optionally substituted $C_1$-$C_{16}$ alkyl radicals optionally interrupted by at least one heteroatom or by at least one group comprising at least one heteroatom, hydroxyl groups, $C_1$-$C_4$ alkoxy groups, $C_2$-$C_4$ (poly)hydroxyalkoxy groups;

alkoxycarbonyl groups (RO—CO—) wherein R is chosen from $C_1$-$C_4$ alkyl radicals, alkylcarbonyloxy radicals (RCO—O—) wherein R is chosen from $C_1$-$C_4$ alkyl radicals;

alkylcarbonyl radicals (R—CO—) wherein R is chosen from $C_1$-$C_4$ alkyl radicals;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O and S and comprising 5 to 7 ring members, which is saturated or unsaturated, aromatic or non-aromatic and is optionally substituted;

alkylcarbonylamino group (RCO—NR'—) wherein the radical R is chosen from $C_1$-$C_4$ alkyl radicals and the radical R' is chosen from hydrogen and $C_1$-$C_4$ alkyl radicals;

aminocarbonyl group ((R)$_2$N—CO—) wherein the radicals R independently of one another are chosen from hydrogen and $C_1$-$C_4$ alkyl radicals;

ureido groups (N(R)$_2$—CO—NR'—) wherein the radicals R and R' independently of one another are chosen from hydrogen and $C_1$-$C_4$ alkyl radicals;

aminosulphonyl group ((R)$_2$N—SO$_2$—) wherein the radicals R independently of one another are chosen from hydrogen or a $C_1$-$C_4$ alkyl radicals;

alkylsulphonylamino groups (RSO$_2$—NR'—) wherein the radicals R and R' independently of one another are chosen from hydrogen and $C_1$-$C_4$ alkyl radicals;

thio groups (HS—);

alkylthio groups (RS—) wherein the radical R are chosen from $C_1$-$C_4$ alkyl radicals;

alkylsulphinyl groups (R—SO—) wherein R are chosen from $C_1$-$C_4$ alkyl radicals;

alkylsulphonyl groups (R—SO$_2$—) wherein R are chosen from $C_1$-$C_4$ alkyl radicals;

nitro groups;

cyano groups; and halogen atoms;

when m' is greater than or equal to 2, two adjacent radicals $R_3$ may form, with the carbon atoms to which they are attached, a secondary ring, aromatic or non-aromatic, comprising 6 ring members, which is optionally substituted by at least one group chosen from the following groups: hydroxyl groups, $C_1$-$C_4$ alkyl groups, $C_1$-$C_4$ alkoxy groups or, $C_2$-$C_4$ (poly)hydroxyalkoxy groups, $C_1$-$C_4$ alkylcarbonylamino groups, amino groups, amino groups substituted by one or two identical or different $C_1$-$C_4$ alkyl radicals which optionally carry at least one hydroxyl group, m' is an integer from 0 to 4; when m' is less than 4, then one or more unsubstituted carbon atom of the aromatic ring carry a hydrogen atom;

$W_1$ radicals, which are identical, are chosen from:
hydrogen,
halogen atoms chosen from bromine, chlorine and fluorine,
—$NR_4$-Ph-$NR_5R_6$, —$NR_4$-Ph-$OR_7$, —O-Ph-$OR_7$ and —O-Ph-$NR_5R_6$ group, where:
$R_4$ and $R_7$, which may be identical or different, are chosen from hydrogen, optionally substituted $C_1$-$C_{20}$ alkyl radicals, optionally substituted aralkyl radicals and optionally substituted phenyl radicals;
$R_5$ and $R_6$, which may be identical or different, are chosen from hydrogen, optionally substituted $C_1$-$C_{20}$ alkyl radicals, optionally substituted phenyl radicals, optionally substituted aralkyl radicals, and an alkylcarbonyl radical (R—CO—) wherein R is a $C_1$-$C_4$ alkyl radical;
$R_5$ and $R_6$ may optionally form, with the nitrogen atom to which they are attached, a heterocycle comprising from 1 to 3 heteroatoms chosen from N, O and S and comprising 5 to 7 ring members, which is saturated or unsaturated, aromatic or non-aromatic and optionally substituted;
Ph is chosen from optionally substituted phenyl radicals;
—$NR_5$—$R_6$ groups, wherein $R_5$ and $R_6$, independently of each other, form, with the carbon atom of the aromatic ring adjacent to that to which —$NR_5R_6$ is attached, a 5- or 6-membered saturated heterocycle;

the radicals $R_1$, which may be identical or different, are chosen from:
optionally substituted $C_1$-$C_4$ alkyl radicals;
optionally substituted phenyl radicals; and
optionally substituted benzyl radicals;

L, a non-cationic linker connecting the two identical azo chromophores, is chosen from:
covalent bonds;
optionally substituted $C_1$-$C_{40}$ alkyl radicals optionally interrupted by a saturated or unsaturated, aromatic or non-aromatic (hetero)cycle comprising 3 to 7 ring members which are optionally substituted and optionally fused, the alkyls radical being optionally interrupted by at least one heteroatom or group comprising at least one heteroatom, with the proviso that the linker L not comprise an azo, nitro, nitroso or peroxo bonds;
optionally substituted phenyl radicals;

the electroneutrality of the compound of formula (I) being ensured by at least one identical or non-identical, cosmetically acceptable anions An.

2. The compounds according to claim 1, wherein the radicals $R_1$ are chosen from:
$C_1$-$C_4$ alkyl radicals which is optionally substituted by at least one radical chosen from hydroxyl, $C_1$-$C_2$ alkoxy, amino and $C_1$-$C_2$ (di)alkylamino radicals;
optionally substituted benzyl radicals.

3. The compounds according to claim 1, wherein the radicals $R_2$, which may be identical or different, are chosen from:
halogen atoms chosen from chlorine and fluorine;
$C_1$-$C_4$ alkyl radicals optionally substituted by at least one radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl and $C_1$-$C_4$ thioalkyl radicals;
phenyl radicals optionally substituted by at least one entities chosen from hydroxyl, $C_1$-$C_2$ alkoxy, $C_2$-$C_4$ (poly)hydroxyalkoxy, amino and $C_1$-$C_2$ (di)alkylamino radicals and halogen atoms;
$C_1$-$C_4$ alkoxy radicals;
$C_1$-$C_4$ alkylsulphonylamino radicals;
$C_2$-$C_4$ (poly)hydroxyalkoxy radicals;
amino radicals;
$C_1$-$C_2$ (di)alkylamino radicals;
$C_2$-$C_4$ (poly)hydroxyalkylamino radicals;
alkylsulphonylamino radicals ($RSO_2N$—) wherein the radical R is chosen from $C_1$-$C_4$ alkyl radicals;
aminosulphonyl radicals (($R)_2NSO_2$—) wherein the radicals R independently of one another are chosen from hydrogen and $C_1$-$C_4$ alkyl radicals;
alkylthio radicals (RS—) wherein the radical R is chosen from $C_1$-$C_4$ alkyl radicals;
alkylsulphinyl radicals (RSO—) wherein the radical R is chosen from $C_1$-$C_4$ alkyl radicals;
alkylsulphonyl radicals (R—$SO_2$—) wherein the radical R is chosen from $C_1$-$C_4$ alkyl radicals;
alkylcarbonylamino radicals (RCONR'—) wherein the radical R is chosen from hydrogen and $C_1$-$C_4$ alkyl radicals and the radical R' is chosen from hydrogen and $C_1$-$C_4$ alkyl radicals.

4. The compounds according to claim 1, wherein the identical or non-identical radicals $R_2$ may optionally form, with the carbon atoms to which they are attached, a secondary, 6-membered aromatic ring optionally substituted by at least one identical or different group chosen from hydroxyl groups, $C_1$-$C_4$ alkyl groups, $C_1$-$C_4$ alkoxy groups, amino groups, and $C_1$-$C_4$ (di)alkyl amino which are identical or different and optionally carry at least one hydroxyl or methylcarbonylamino groups.

5. The compounds according to claim 1, wherein the radicals $R_3$, which are identical or different, are chosen from:
optionally substituted $C_1$-$C_{16}$ alkyl radicals;
halogen atoms;
hydroxyl groups;
$C_1$-$C_2$ alkoxy radicals;
$C_2$-$C_4$ (poly)hydroxyalkoxy radicals;
amino radicals;
amino radicals substituted by one or two identical or different $C_1$-$C_4$ alkyl radicals which optionally carry at least one hydroxyl group or at least one $C_1$-$C_4$ alkoxy radical, it being possible for the two alkyl radicals to form, with the nitrogen atom to which they are attached, a heterocycle comprising from 1 to 3 heteroatoms chosen from N, O and S the heterocycle comprising 5 to 7 ring members, being saturated or unsaturated, aromatic or non-aromatic, and optionally substituted;
alkylcarbonylamino radicals (RCO—NR'—) wherein the radical R is chosen from $C_1$-$C_4$ alkyl radicals and the radical R' is chosen from hydrogen and $C_1$-$C_4$ alkyl radicals;
alkylsulphonylamino radicals (R'$SO_2$—NR—) wherein the radical R is chosen from hydrogen and $C_1$-$C_4$ alkyl radicals and the radical R' is chosen from $C_1$-$C_4$ alkyl radicals;
aminosulphonyl radicals (($R)_2N$—$SO_2$—) wherein the radicals R, which are identical or not, are chosen from hydrogen and $C_1$-$C_4$ alkyl radicals;
alkylthio radicals (RS—) wherein the radical R is chosen from $C_1$-$C_4$ alkyl radicals; and
alkylsulphonyl radicals (R—$SO_2$—) wherein the radical R is chosen from $C_1$-$C_4$ alkyl radicals.

6. The compounds according to claim 1, wherein the radicals $R_3$, which are identical or different, are chosen from:
$C_1$-$C_4$ alkyl radicals which are optionally substituted by at least one radical chosen from hydroxyl radicals, $C_1$-$C_2$ alkylcarbonylamino radicals, amino radicals substituted by two identical or different $C_1$-$C_2$ alkyl radicals which optionally carry at least one entity chosen from hydroxyl groups and $C_1$-$C_2$ alkoxy radicals, it being possible for these two alkyl radicals optionally to form, with the nitrogen atom to which they are attached, a 5- or 6-membered heterocycle which is saturated or unsaturated and optionally aromatic;

$C_2$-$C_4$ hydroxyalkoxy radicals;

halogen atoms chosen from chlorine and fluorine;

amino radicals;

amino radicals substituted by one or two identical or different $C_1$-$C_2$ alkyl radicals which optionally carry at least one hydroxyl group;

methylcarbonylamino radicals;

methylsulphonylamino radicals;

hydroxyl radicals;

$C_1$-$C_2$ alkoxy radicals; and methylsulphonyl radicals.

7. The compounds according to claim 1, wherein when the coefficient m' is greater than or equal to 2, two adjacent radicals $R_3$ may form, with the carbon atoms to which they are attached, a secondary, 6-membered, aromatic ring optionally substituted by at least one group chosen from hydroxyl groups, $C_1$-$C_4$ alkyl radicals, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl-type radicals which optionally carry at least one entity chosen from hydroxyl groups, —$NR_4$-Ph radicals, —$NR_4$-Ph-$NR_5R_6$ radicals, and —$NR_4$-Ph-$OR_7$ radicals.

8. The compounds according to claim 7, wherein the two adjacent radicals $R_3$ may form, with the carbon atoms to which they are attached, a secondary, 6-membered, aromatic ring which is optionally substituted by at least one group chosen from hydroxyl groups, methoxy groups, ethoxy groups, 2-hydroxyethyloxy groups, amino groups, methylcarbonylamino groups, (di)-2-hydroxyethylamino groups, —NH-Ph groups, —NH-Ph-$NH_2$ groups, —NH-Ph-NH-$COCH_3$ groups, —NH-Ph-OH groups, and —NH-Ph-$OCH_3$ groups.

9. The compounds according to claim 1, wherein $R_4$ and $R_7$ independently of one another are chosen from:

hydrogen;

$C_1$-$C_6$ alkyl radicals which are optionally substituted; and aryl and arylalkyl radicals, the aryl moiety being optionally substituted.

10. The compounds according to claim 1, wherein the radicals $R_5$ and $R_6$, which are identical or different, are chosen from:

hydrogen;

alkylcarbonyl radicals (R—CO—) wherein R is chosen from optionally substituted $C_1$-$C_4$ alkyl radicals; and $C_1$-$C_6$ alkyl radicals which is optionally substituted by at least one identical or different group chosen from hydroxyl groups, $C_1$-$C_2$ alkoxy groups, amino groups, and $C_1$-$C_4$ (di)alkylamino group groups; the alkyl radical may further be substituted by at least one identical or different group chosen from $C_1$-$C_4$ alkylsulphonyl groups, $C_1$-$C_4$ alkylsulphinyl groups, and $C_1$-$C_4$ alkylcarbonyl groups; and aryl and arylalkyl radicals, the aryl moiety being optionally substituted.

11. The compounds according to claim 1, wherein the radicals $R_5$ and $R_6$, which are identical or different, are chosen from:

hydrogen;

methylcarbonyl, ethylcarbonyl and propylcarbonyl radicals;

optionally substituted $C_1$-$C_3$ alkyl radicals; and phenyl radicals which are optionally substituted by at least one radical chosen from hydroxyl radicals, $C_1$-$C_2$ alkoxy radicals, amino radicals, amino radicals substituted by at least one $C_1$-$C_4$ group which optionally carry at least one hydroxyl group.

12. The compounds according to claim 1, wherein the radicals $R_5$ and $R_6$ form, together with the nitrogen atom to which each is attached, a heterocycle comprising from 1 to 3 heteroatoms chosen from N, O and S and comprising 5 to 7 ring members, which is saturated or unsaturated, aromatic or non-aromatic, and optionally substituted.

13. The compounds according to claim 12, wherein the heterocycle comprising 5 to 7 ring members is chosen from the following heterocycles: piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, 1-methyl-4-propylpyrrole.

14. The compounds according to claim 1, wherein the radicals $R_5$ and $R_6$ are chosen from alkyl radicals which, independently of one another, form, with the carbon atom of the aromatic ring optionally substituted by a hydroxyl and adjacent to that to which —$NR_5R_6$ is attached, a 5- or 6-membered saturated heterocycle.

15. The compounds according to claim 1, wherein L is chosen from

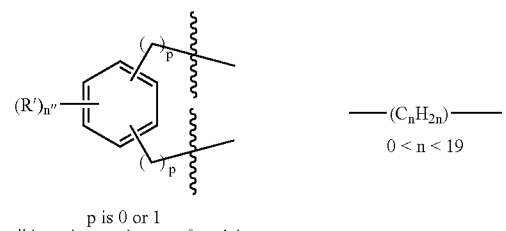

p is 0 or 1
n'' is an integer between 0 and 4

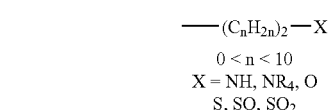

0 < n < 10
X = NH, $NR_4$, O
S, SO, $SO_2$

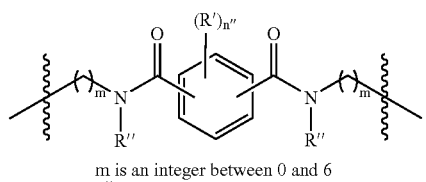

m is an integer between 0 and 6
n'' is an integer between 0 and 4

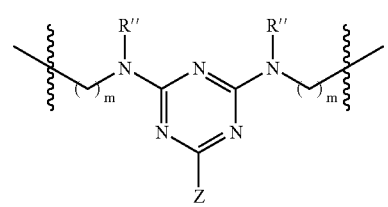

m is an integer between 0 and 6
Z = OH, $NR_8R_9$

-continued

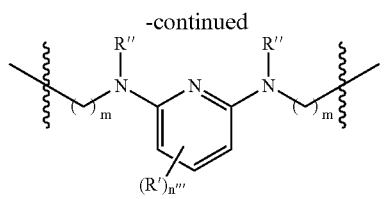

m is an integer between 0 and 6
n''' is an integer between 0 and 3 wherein formulae:
R' has the same definition as $R_3$;
R'' radicals, which are identical, are chosen from hydrogen and $C_1$-$C_4$ alkyl radicals;
$R_8$ and $R_9$ are chosen from, independently of one another, hydrogen and $C_1$-$C_8$ alkyl radicals which are optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino and optionally substituted phenyl radicals.

16. The compounds according to claim 1, wherein the anion An is chosen from an organic or inorganic anion or anion mixture allowing the charge or charges on the compounds of formula (I) to be balanced, and chosen from halides; hydroxides; sulphates; hydrogensulphates; alkylsulphates for which the linear or branched alkyl moiety is $C_1$-$C_6$; carbonates and hydrogencarbonates; salts of carboxylic acids; alkylsulphonates for which the linear or branched alkyl moiety is $C_1$-$C_6$; arylsulphonates for which the aryl moiety is optionally substituted by at least one $C_1$-$C_4$ alkyl radical; and alkylsulphonyls.

17. The compounds according to claim 1, wherein the compounds correspond to formula (I') below, and also their resonance forms, their acid addition salts or their solvates:

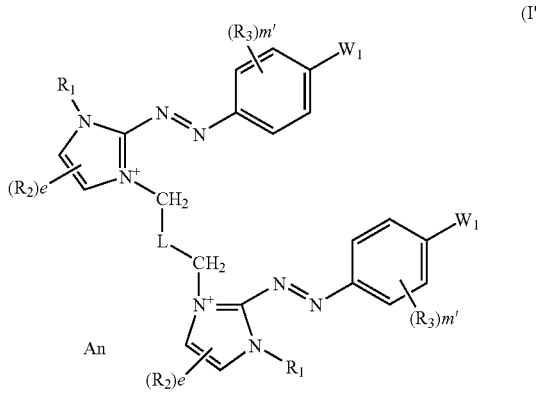

the $W_1$ groups defined as radicals, which are identical, are chosen from:
hydrogen,
halogen atoms chosen from bromine, chlorine and fluorine,
—$NR_4$-Ph-$NR_5R_6$, —$NR_4$-Ph-$OR_7$, —O-Ph-$OR_7$ and —O-Ph-$NR_5R_6$ groups, where:
$R_4$ and $R_7$, which are identical or not, are chosen from hydrogen atoms, optionally substituted $C_1$-$C_{20}$ alkyl radicals, optionally substituted aralkyl radicals and optionally substituted phenyl radicals;
$R_5$ and $R_6$, which are identical or not, are chosen from hydrogen, optionally substituted $C_1$-$C_{20}$ alkyl radicals, optionally substituted phenyl radicals, optionally substituted aralkyl radicals, and alkylcarbonyl radicals (R—CO—) wherein R is chosen from $C_1$-$C_4$ alkyl radicals;
$R_5$ and $R_6$ may optionally form, with the nitrogen atom to which they are attached, a heterocycle comprising from 1 to 3 heteroatoms chosen from N, O and S and comprising 5 to 7 ring members, which is saturated or unsaturated, aromatic or non-aromatic and optionally substituted;
Ph is chosen from optionally substituted phenyl radicals;
—$NR_5$—$R_6$ groups, wherein $R_5$ and $R_6$, independently of each other, form, with the carbon atom of the aromatic ring adjacent to that to which —$NR_5R_6$ is attached, a 5- or 6-membered saturated heterocycle, the radical $R_1$ defined as the radicals, which are identical or not, are chosen from: optionally substituted $C_1$-$C_4$ alkyl radicals; optionally substituted phenyl radicals; and optionally substituted benzyl radicals,
radicals $R_2$, which may be identical or different, are chosen from:
optionally substituted $C_1$-$C_{16}$ alkyl radicals optionally interrupted by at least one heteroatom and/or by at least one group comprising at least one heteroatom chosen from oxygen, nitrogen, sulphur, —CO—, —$SO_2$— or combinations thereof, the alkyl radicals being further optionally substituted by at least one group chosen from thio (—SH), $C_1$-$C_4$ thioalkyl; $C_1$-$C_4$ alkylsulphinyl or $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals,
alkylcarbonyl radicals (R—CO—) wherein R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O and S and 5 to 7 ring members, which is saturated or unsaturated, aromatic or non-aromatic and optionally substituted;
alkylcarbonylamino groups (RCO—NR'—) wherein the radical R is chosen from a $C_1$-$C_4$ alkyl radicals and the radical R' is chosen from hydrogen and $C_1$-$C_4$ alkyl radicals;
aminocarbonyl groups (($R)_2$N—CO—) wherein the radicals R independently of one another are chosen from hydrogen and $C_1$-$C_4$ alkyl radicals;
ureido groups (N($R)_2$—CO—NR'—) wherein the radicals R and R' independently of one another are chosen from hydrogen and $C_1$-$C_4$ alkyl radicals;
aminosulphonyl groups (($R)_2$N—$SO_2$—) wherein the radicals R independently of one another are chosen from hydrogen and $C_1$-$C_4$ alkyl radicals;
alkylsulphonylamino group ($RSO_2$—NR'—) wherein R is chosen from a $C_1$-$C_4$ alkyl radicals and R' is chosen from hydrogen and $C_1$-$C_4$ alkyl radicals;
optionally substituted aryl radicals;
optionally substituted ($C_1$-$C_4$) alkylaryl radicals;

alkylsulphinyl groups (R—SO—) wherein R is chosen from $C_1$-$C_4$ alkyl radicals;
alkylsulphonyl groups (R—$SO_2$—) wherein R is chosen from $C_1$-$C_4$ alkyl radicals;
nitro groups;
cyano groups;
halogen atoms;
thio groups (HS—); and
alkylthio groups (RS—) wherein the radical R is chosen from optionally substituted $C_1$-$C_4$ alkyl radicals;
and $R_3$ being defined as the radicals $R_3$, which may be identical or different, are chosen from:
optionally substituted $C_1$-$C_{16}$ alkyl radicals optionally interrupted by at least one heteroatom or by at least one group comprising at least one heteroatom,
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals;
alkylcarbonyl radicals (R—CO—) wherein R is chosen from $C_1$-$C_4$ alkyl radicals;
amino groups;
amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O and S and comprising 5 to 7 ring members, which is saturated or unsaturated, aromatic or non-aromatic and is optionally substituted;
alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;
aminocarbonyl groups ($(R)_2$N—CO—) wherein the radicals R independently of one another are chosen from hydrogen and $C_1$-$C_4$ alkyl radicals;
ureido groups ($N(R)_2$—CO—NR'—) wherein the radicals R and R' independently of one another are chosen from hydrogen and $C_1$-$C_4$ alkyl radicals;
aminosulphonyl groups ($(R)_2$N—$SO_2$—) wherein the radicals R independently of one another are chosen from hydrogen and $C_1$-$C_4$ alkyl radicals;
alkylsulphonylamino groups ($RSO_2$—NR'—) wherein the radicals R and R' independently of one another are chosen from hydrogen and $C_1$-$C_4$ alkyl radicals;
thio groups (HS—);
alkylthio groups (RS—) wherein the radical R are chosen from $C_1$-$C_4$ alkyl radicals;
alkylsulphinyl groups (R—SO—) wherein R are chosen from $C_1$-$C_4$ alkyl radicals;
alkylsulphonyl groups (R—$SO_2$—) wherein R are chosen from $C_1$-$C_4$ alkyl radicals;
nitro groups;
cyano groups; and
halogen atoms;
and the coefficient e is an integer from 0 to 2; when e is less than 2, one or more unsubstituted carbon atom(s) of the heterocycle carry a hydrogen atom and m' is an integer from 0 to 4; when m' is less than 4, then one or more unsubstituted carbon atom of the aromatic ring carry a hydrogen atom.

18. The compounds according to claim 1, wherein the compounds correspond to the following formulae, to their addition salts with an acid, or to their solvates:

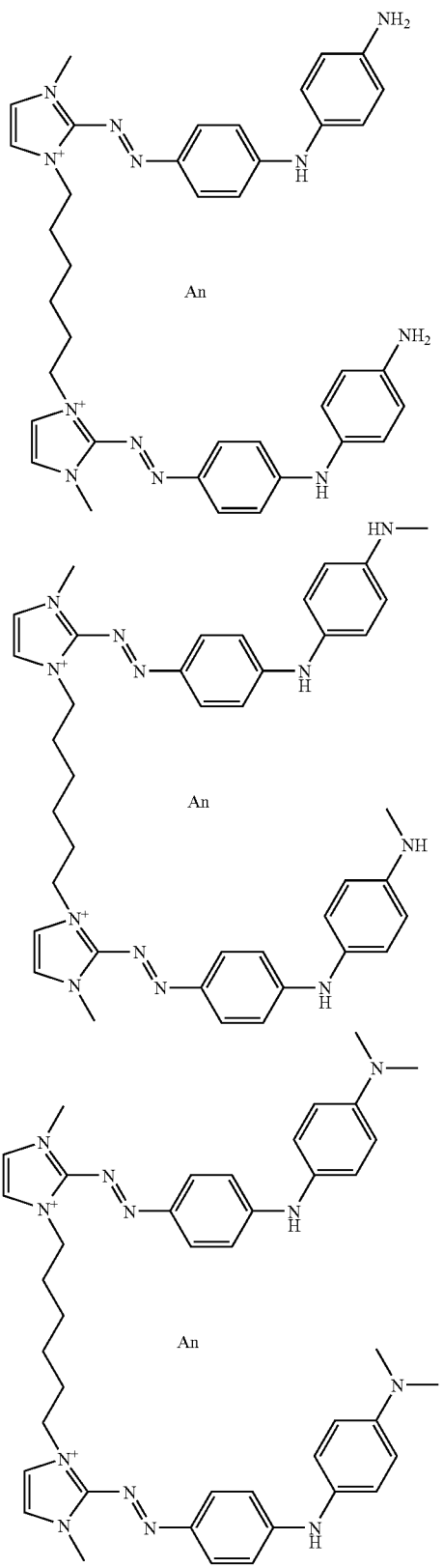

57
-continued
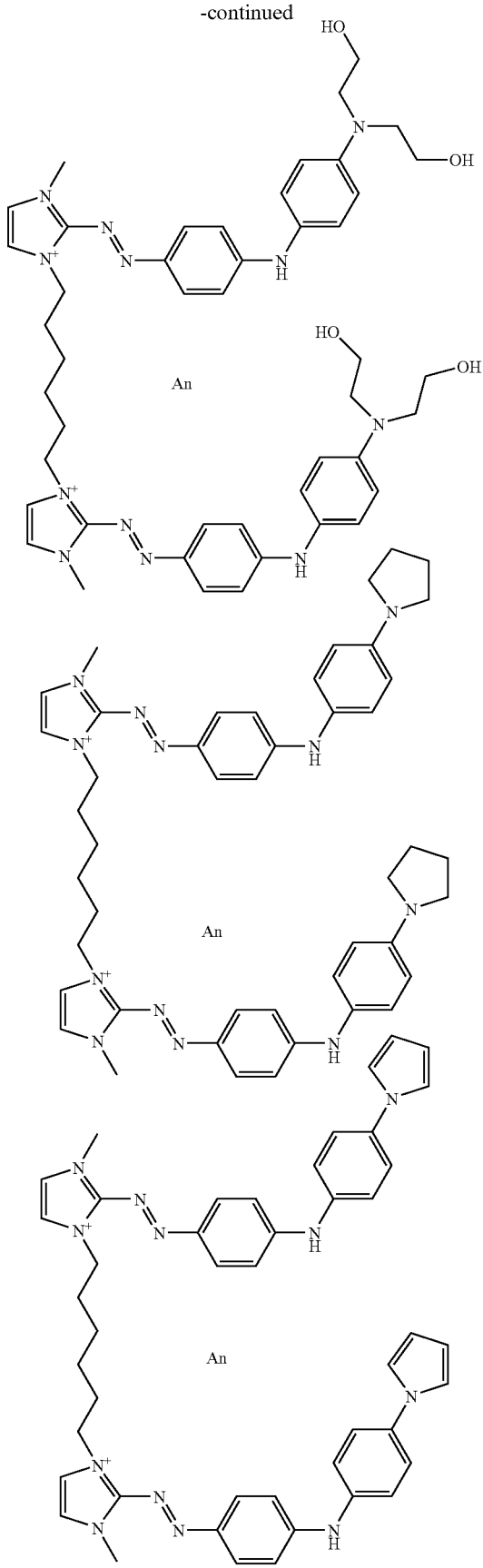
58
-continued
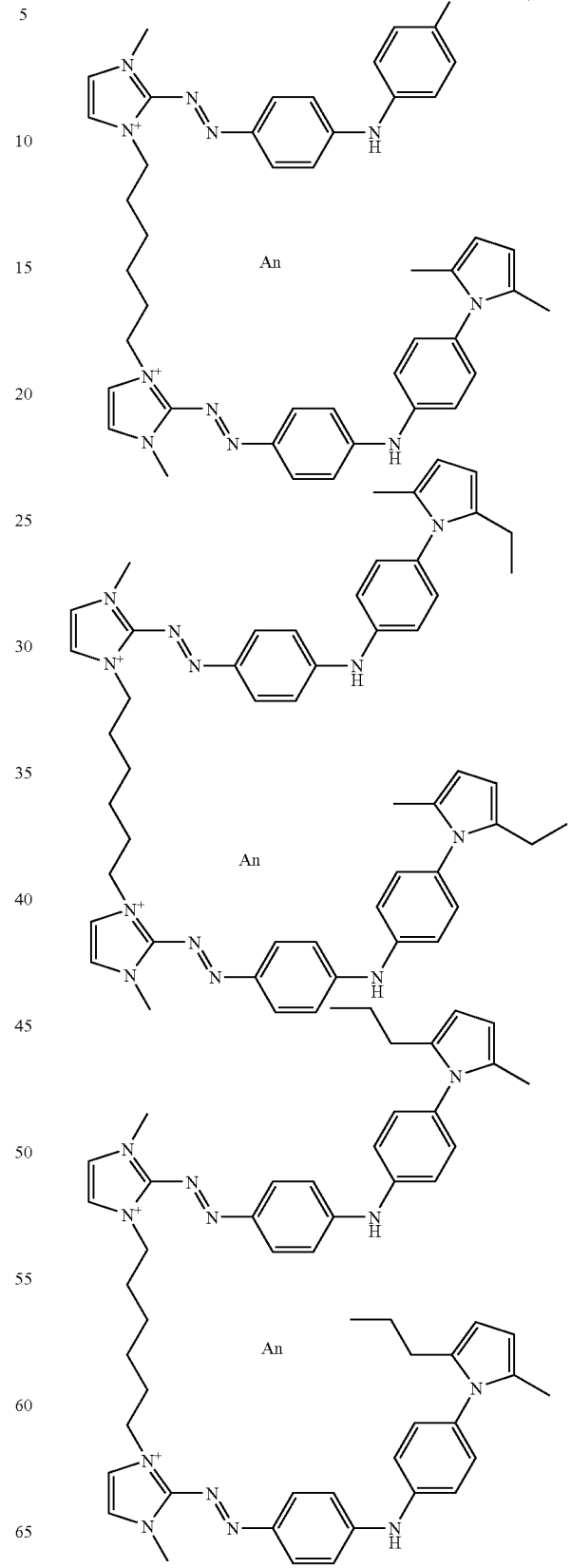

-continued
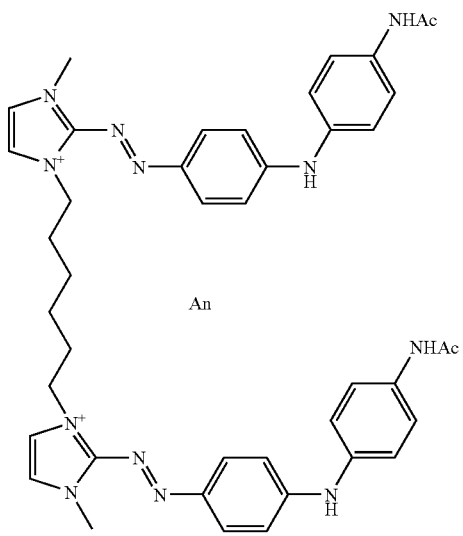
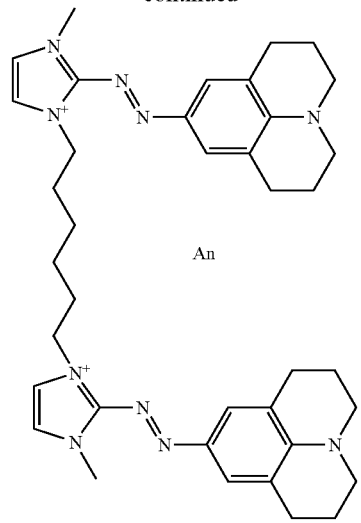
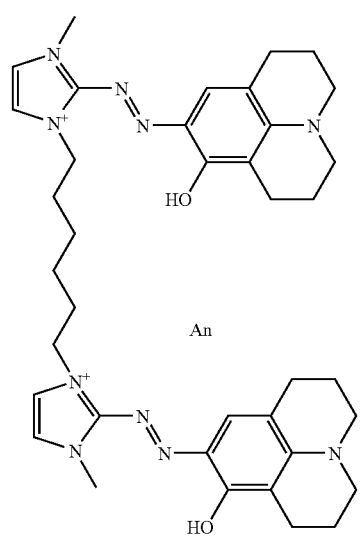
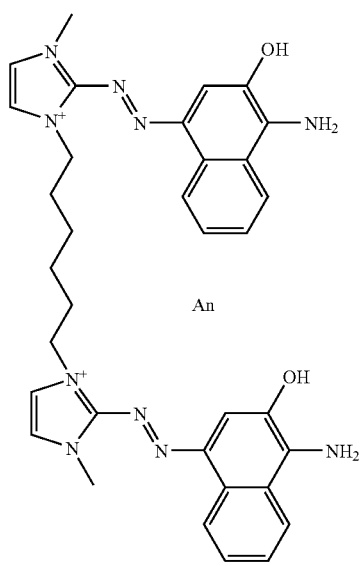

-continued
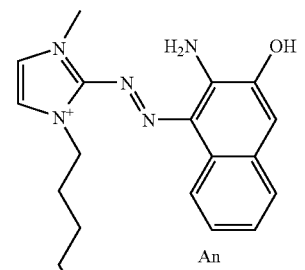
An
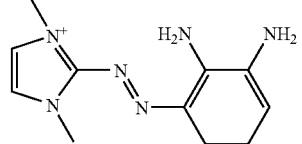
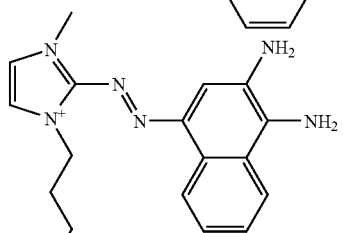
An
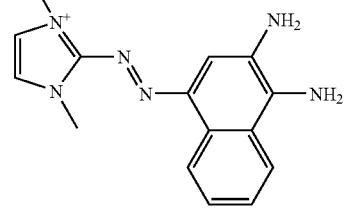
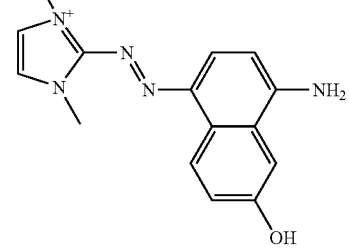
An
-continued
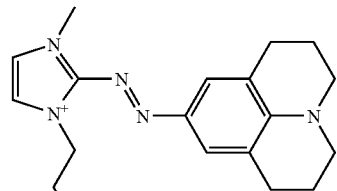
An
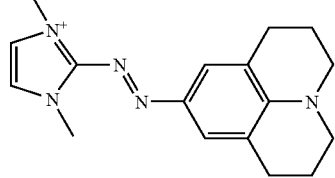
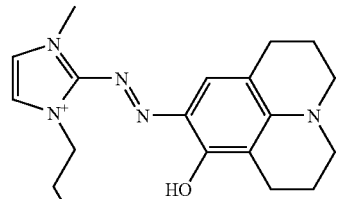
An
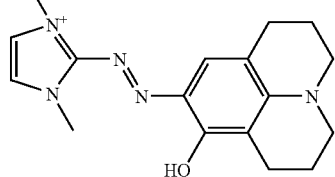
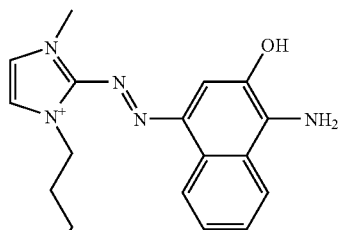
An
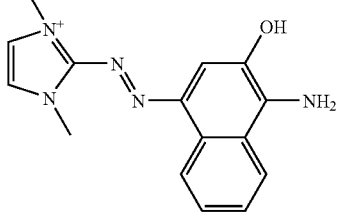

-continued
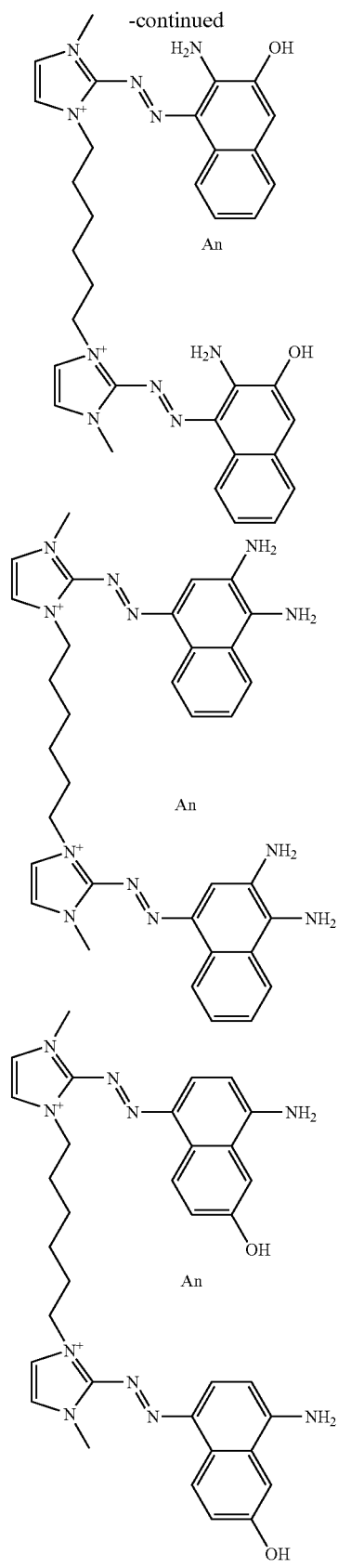
-continued

65
-continued
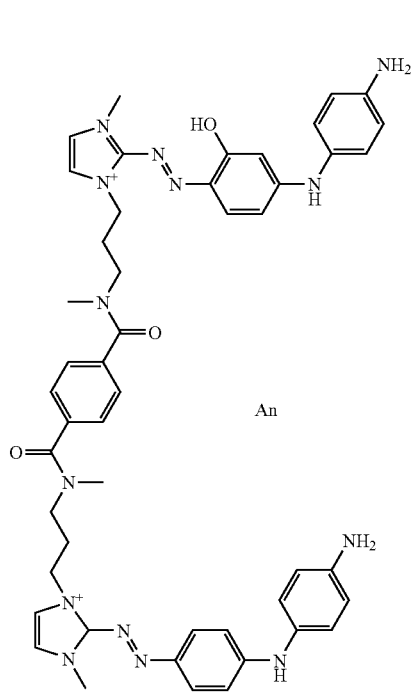
66
-continued
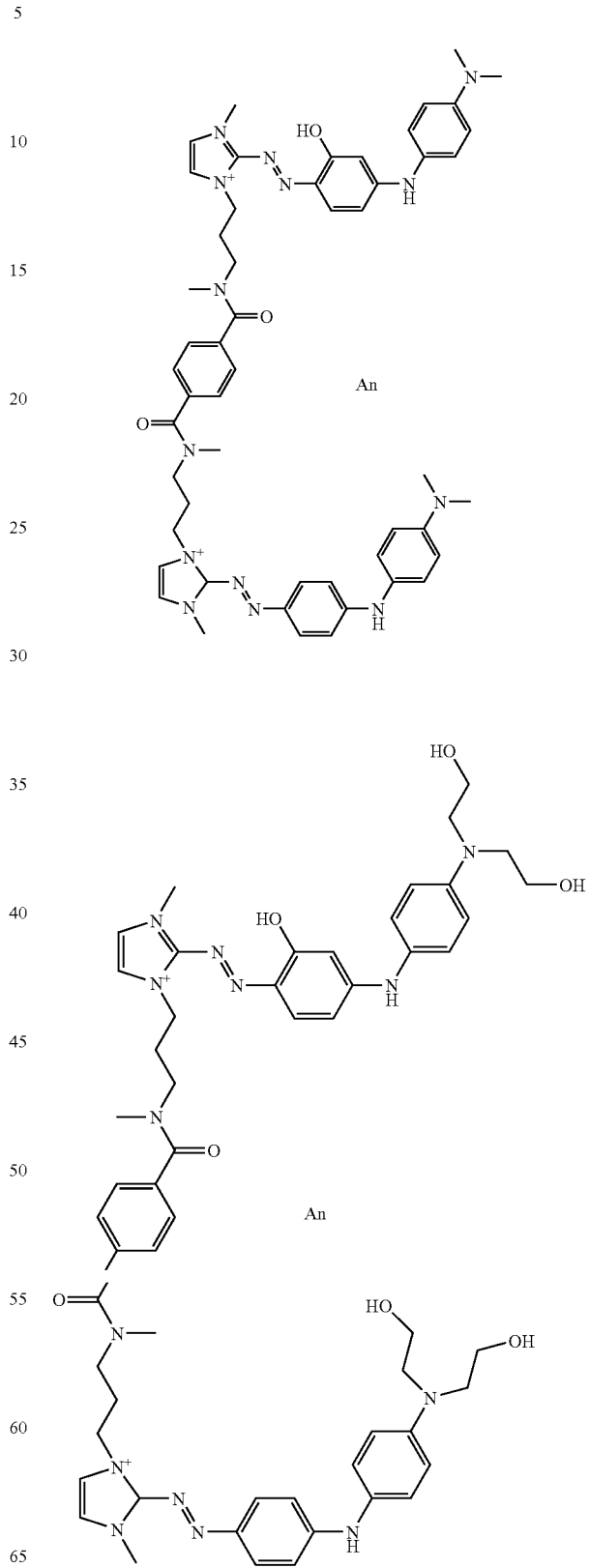

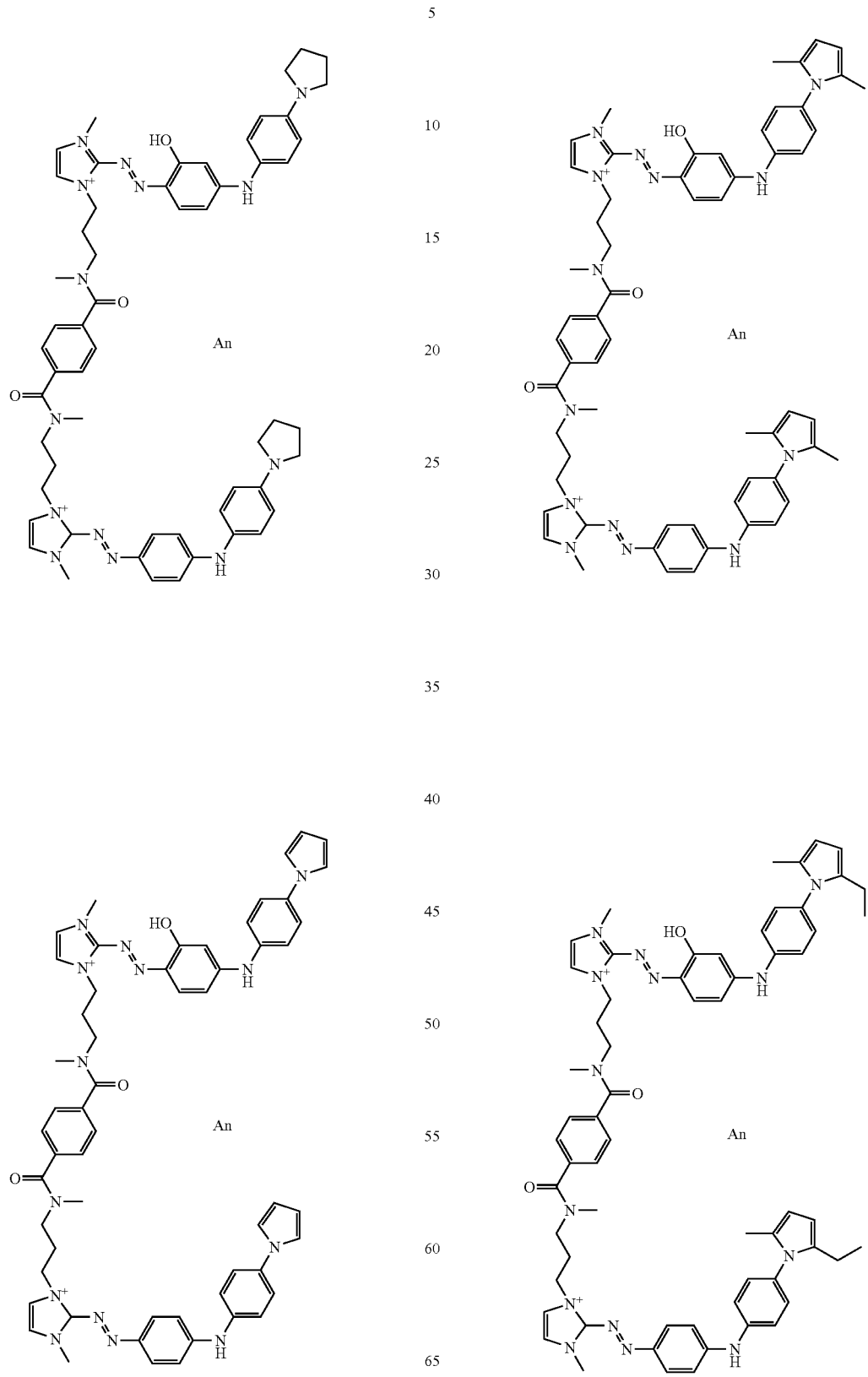

69
-continued
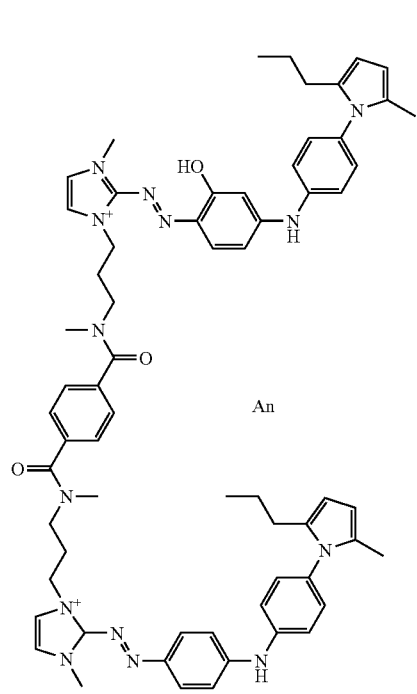
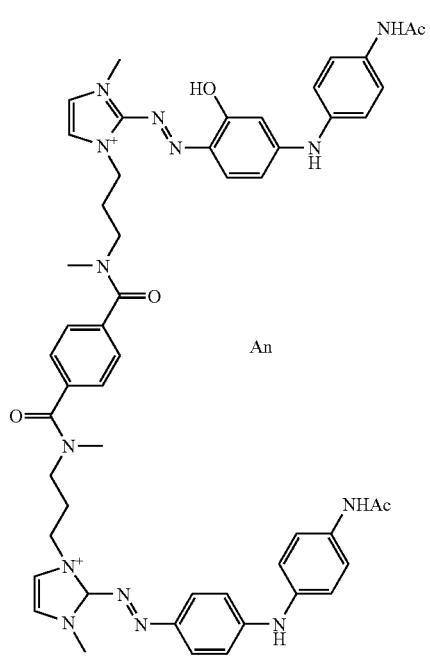
70
-continued
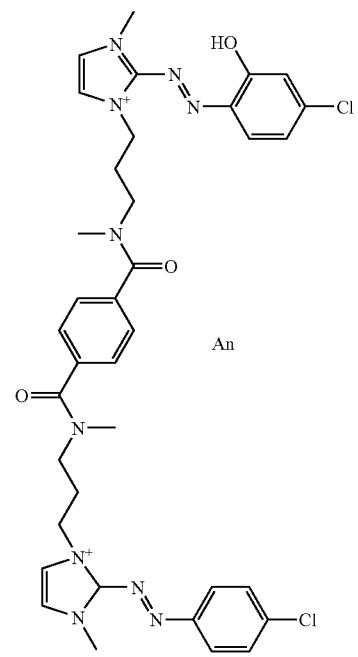
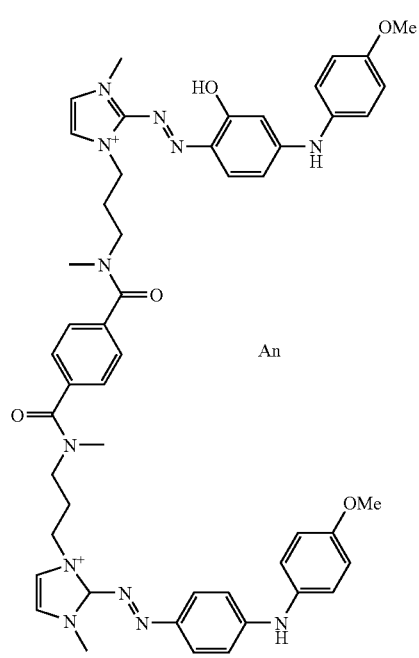

71
-continued
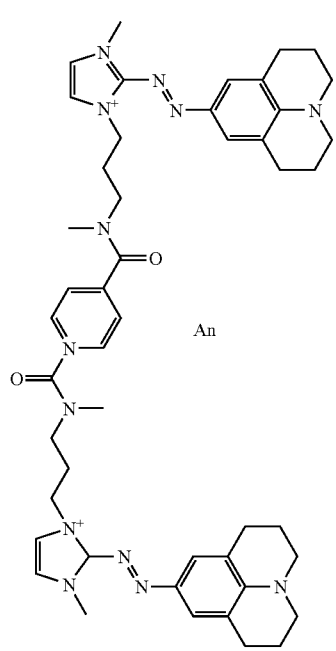
An
72
-continued
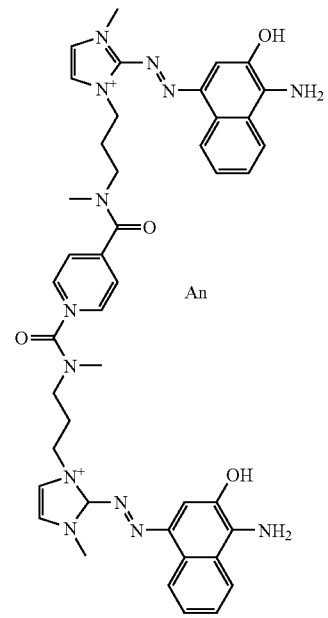
An
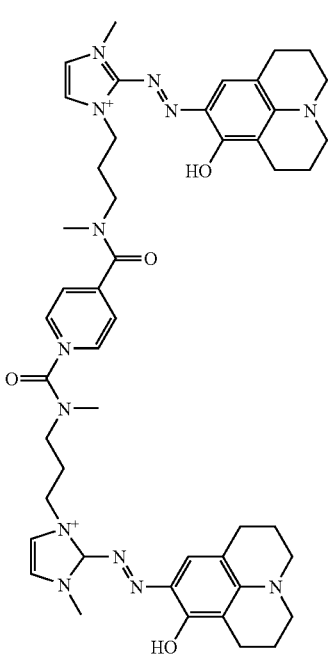
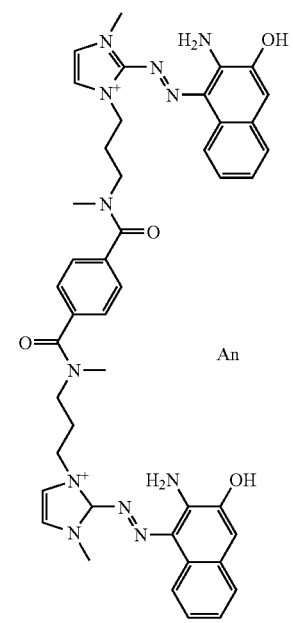
An -continued
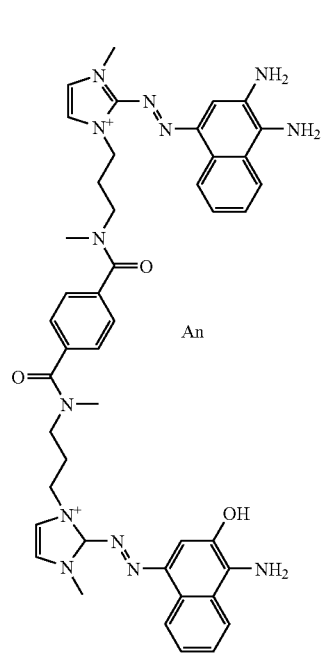
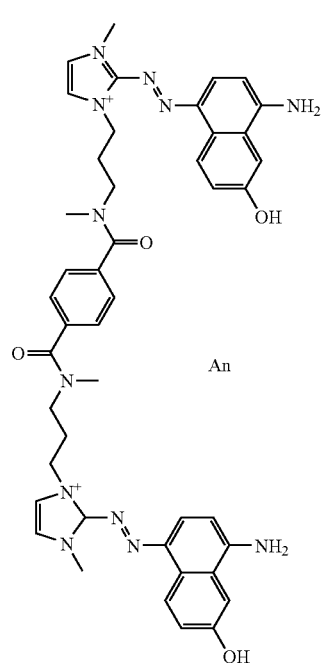
-continued
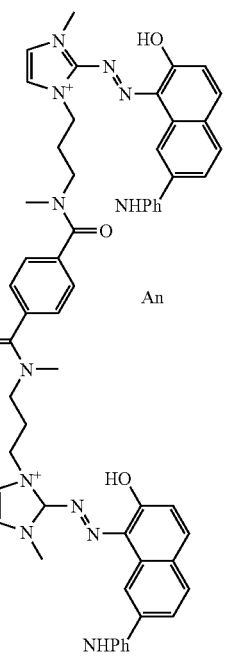
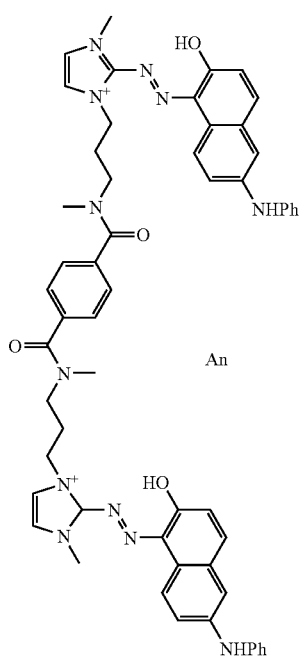
wherein An is defined as cosmetically acceptable anions.
19. A dyeing composition comprising, in a medium appropriate for the dyeing of keratin fibers, as direct dye at least one compound of formula (I), or its acid addition salts,

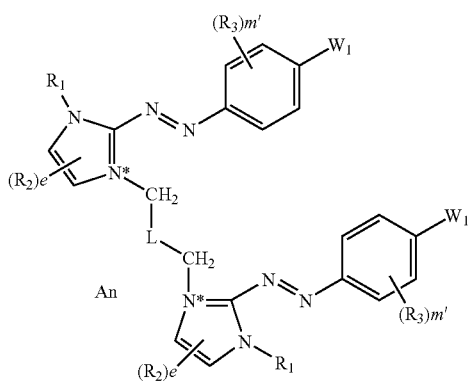

(I)

wherein:

the radicals $R_1$, which are identical or not, are chosen from:
optionally substituted $C_1$-$C_4$ alkyl radicals;
optionally substituted phenyl radicals; and
optionally substituted benzyl radicals;

the radicals $R_2$, which may be identical or different, are chosen from:
optionally substituted $C_1$-$C_{16}$ alkyl radicals optionally interrupted by at least one entity chosen from heteroatom and groups comprising at least one heteroatom, the alkyl radical being further optionally substituted by at least one group chosen from thio (—SH), $C_1$-$C_4$ thioalkyl; $C_1$-$C_4$ alkylsulphinyl or $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals,
alkylcarbonyl radicals (R—CO—) wherein R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O and S and 5 to 7 ring members, which is saturated or unsaturated, aromatic or non-aromatic and optionally substituted;
alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;
aminocarbonyl groups ((R)$_2$N—CO—) wherein the radicals R independently of one another are chosen from hydrogen and $C_1$-$C_4$ alkyl radicals;
ureido groups (N(R)$_2$—CO—NR'—) wherein the radicals R and R' independently of one another are chosen from hydrogen and $C_1$-$C_4$ alkyl radicals;
aminosulphonyl groups ((R)$_2$N—SO$_2$—) wherein the radicals R independently of one another are chosen from hydrogen and $C_1$-$C_4$ alkyl radicals;
alkylsulphonylamino groups (RSO$_2$—NR'—) wherein R is chosen from $C_1$-$C_4$ alkyl radicals and R' is chosen from hydrogen and $C_1$-$C_4$ alkyl radicals;
optionally substituted aryl radicals;
optionally substituted ($C_1$-$C_4$) alkylaryl radicals;
alkylsulphinyl groups (R—SO—) wherein R is chosen from $C_1$-$C_4$ alkyl radicals;
alkylsulphonyl groups (R—SO$_2$—) wherein R is chosen from $C_1$-$C_4$ alkyl radicals;
nitro groups;
cyano groups;
halogen atoms;
thio groups (HS—); and
alkylthio groups (RS—) wherein the radical R is chosen from optionally substituted $C_1$-$C_4$ alkyl radicals;
when e is 2, the two radicals $R_2$ may optionally form, with the carbon atoms to which they are attached, a secondary ring, aromatic or non-aromatic, comprising 5 or 6 ring members which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

e is an integer from 0 to 2; when e is less than 2, one or more unsubstituted carbon atom(s) of the heterocycle carry a hydrogen atom, the radicals $R_3$, which may be identical or different, are chosen from:
optionally substituted $C_1$-$C_{16}$ alkyl radicals optionally interrupted by at least one heteroatom or by at least one group comprising at least one heteroatom, hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals;
alkylcarbonyl radicals (R—CO—) wherein R is chosen from $C_1$-$C_4$ alkyl radicals;
amino groups;
amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O and S and comprising 5 to 7 ring members, which is saturated or unsaturated, aromatic or non-aromatic and is optionally substituted;
alkylcarbonylamino group (RCO—NR'—) wherein the radical R is chosen from $C_1$-$C_4$ alkyl radicals and the radical R' is chosen from hydrogen and $C_1$-$C_4$ alkyl radicals;
aminocarbonyl group ((R)$_2$N—CO—) wherein the radicals R independently of one another are chosen from hydrogen and $C_1$-$C_4$ alkyl radicals;
ureido groups (N(R)$_2$—CO—NR'—) wherein the radicals R and R' independently of one another are chosen from hydrogen and $C_1$-$C_4$ alkyl radicals;
aminosulphonyl group ((R)$_2$N—SO$_2$—) wherein the radicals R independently of one another are chosen from hydrogen or a $C_1$-$C_4$ alkyl radicals;
alkylsulphonylamino groups (RSO$_2$—NR'—) wherein the radicals R and R' independently of one another are chosen from hydrogen and $C_1$-$C_4$ alkyl radicals;
thio groups (HS—);
alkylthio groups (RS—) wherein the radical R are chosen from $C_1$-$C_4$ alkyl radicals;

alkylsulphinyl groups (R—SO—) wherein R are chosen from $C_1$-$C_4$ alkyl radicals;
alkylsulphonyl groups (R—SO$_2$—) wherein R are chosen from $C_1$-$C_4$ alkyl radicals;
nitro groups;
cyano groups; and
halogen atoms;
when m' is greater than or equal to 2, two adjacent radicals $R_3$ may form, with the carbon atoms to which they are attached, a secondary ring, aromatic or non-aromatic, comprising 6 ring members, which is optionally substituted by at least one group chosen from the following groups: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups or, amino groups substituted by one or two identical or different $C_1$-$C_4$ alkyl radicals which optionally carry at least one hydroxyl group,
m' is an integer from 0 to 4; when m' is less than 4, then one or more unsubstituted carbon atom of the aromatic ring carry a hydrogen atom;
$W_1$ radicals, which are identical, are chosen from:
hydrogen,
halogen atoms chosen from bromine, chlorine and fluorine,
—NR$_4$-Ph-NR$_5$R$_6$, —NR$_4$-Ph-OR$_7$, —O-Ph-OR$_7$ and —O-Ph-NR$_5$R$_6$ group, where:
$R_4$ and $R_7$, which may be identical or different, are chosen from hydrogen, optionally substituted $C_1$-$C_{20}$ alkyl radicals, optionally substituted aralkyl radicals and optionally substituted phenyl radicals;
$R_5$ and $R_6$, which may be identical or different, are chosen from hydrogen, optionally substituted $C_1$-$C_{20}$ alkyl radicals, optionally substituted phenyl radicals, optionally substituted aralkyl radicals, and an alkylcarbonyl radical (R—CO—) wherein R is a $C_1$-$C_4$ alkyl radical;
$R_5$ and $R_6$ may optionally form, with the nitrogen atom to which they are attached, a heterocycle comprising from 1 to 3 heteroatoms chosen from N, O and S and comprising 5 to 7 ring members, which is saturated or unsaturated, aromatic or non-aromatic and optionally substituted;
Ph is chosen from optionally substituted phenyl radicals;
—NR$_5$—R$_6$ groups, wherein R$_5$ and R$_6$, independently of each other, form, with the carbon atom of the aromatic ring adjacent to that to which —NR$_5$R$_6$ is attached, a 5- or 6-membered saturated heterocycle;
the radicals $R_1$, which may be identical or different, are chosen from:
optionally substituted $C_1$-$C_4$ alkyl radicals;
optionally substituted phenyl radicals; and
optionally substituted benzyl radicals;
L, a non-cationic linker connecting the two identical azo chromophores, is chosen from:
covalent bonds;
optionally substituted $C_1$-$C_{40}$ alkyl radicals optionally interrupted by a saturated or unsaturated, aromatic or non-aromatic (hetero)cycle comprising 3 to 7 ring members which are optionally substituted and optionally fused, the alkyls radical being optionally interrupted by at least one heteroatom or group comprising at least one heteroatom, with the proviso that the linker L not comprise an azo, nitro, nitroso or peroxo bonds;
optionally substituted phenyl radicals;

the electroneutrality of the compound of formula (I) being ensured by at least one identical or non-identical, cosmetically acceptable anions An.

20. The composition according to claim 19, wherein the amount of the at least one compound of formula (I) is present in an amount ranging from 0.001% to 20% by weight relative to the total weight of the dyeing composition.

21. The composition according to claim 19, wherein the composition comprises at least one additional direct dye, at least one oxidation base optionally in combination with at least one coupler, or mixtures thereof.

22. The composition according to claim 21, wherein the additional direct dye is chosen from cationic and nonionic dyes chosen from nitrobenzene, azo, azomethine, methine, tetraazapentamethine, anthraquinone, naphthoquinone, benzoquinone, phenothiazine, indigoid, xanthene, phenanthridine, and phthalocyanine dyes, dyes derived from triarylmethane, natural dyes, and mixtures thereof.

23. The composition according to claim 21, wherein the at least one oxidation base is chosen from p-phenylenediamines, bisphenylalkylenediamines, o-aminophenols, p-aminophenols and heterocyclic bases.

24. The composition according to claim 21, wherein the coupler is chosen from m-aminophenols, m-phenylenediamines, m-diphenols, naphthols and heterocyclic couplers.

25. The composition according to claim 19, wherein the composition comprises at least one oxidizing agent.

26. A method of coloring keratin fibers comprising contacting the fibers, which are dry or wet, with a symmetrical cationic diazo compound chosen from those of formula (I) below, their resonance forms, and their acid addition salts and their solvates:

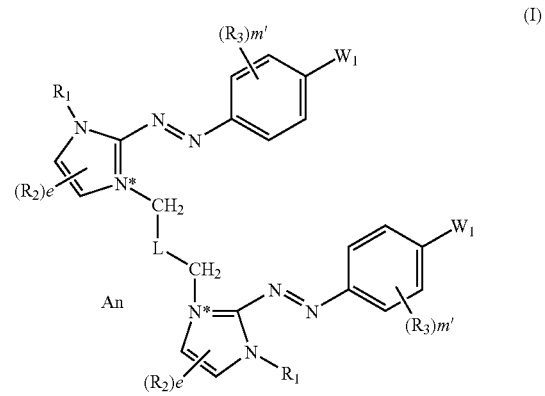

(I)

wherein:
the radicals $R_1$, which are identical or not, are chosen from:
optionally substituted $C_1$-$C_4$ alkyl radicals;
optionally substituted phenyl radicals; and
optionally substituted benzyl radicals;
the radicals $R_2$, which may be identical or different, are chosen from:
optionally substituted $C_1$-$C_{16}$ alkyl radicals optionally interrupted by at least one entity chosen from heteroatom and groups comprising at least one heteroatom, the alkyl radical being further optionally substituted by at least one group chosen from thio (—SH), $C_1$-$C_4$ thioalkyl; $C_1$-$C_4$ alkylsulphinyl or $C_1$-$C_4$ alkylsulphonyl groups;
hydroxyl groups,
$C_1$-$C_4$ alkoxy groups, $C_2$-$C_4$ (poly)hydroxyalkoxy groups;

alkoxycarbonyl groups (RO—CO—) wherein R is chosen from $C_1$-$C_4$ alkyl radicals, alkylcarbonyloxy radicals (RCO—O—) wherein R is chosen from $C_1$-$C_4$ alkyl radicals, alkylcarbonyl radicals (R—CO—) wherein R is chosen from $C_1$-$C_4$ alkyl radicals, amino groups, amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O and S and 5 to 7 ring members, which is saturated or unsaturated, aromatic or non-aromatic and optionally substituted;

alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;

aminocarbonyl groups ((R)$_2$N—CO—) wherein the radicals R independently of one another are chosen from hydrogen and $C_1$-$C_4$ alkyl radicals;

ureido groups (N(R)$_2$—CO—NR'—) wherein the radicals R and R' independently of one another are chosen from hydrogen and $C_1$-$C_4$ alkyl radicals;

aminosulphonyl groups ((R)$_2$N—SO$_2$—) wherein the radicals R independently of one another are chosen from hydrogen and $C_1$-$C_4$ alkyl radicals;

alkylsulphonylamino groups (RSO$_2$—NR'—) wherein R is chosen from $C_1$-$C_4$ alkyl radicals and R' is chosen from hydrogen and $C_1$-$C_4$ alkyl radicals;

optionally substituted aryl radicals;

optionally substituted ($C_1$-$C_4$)alkylaryl radicals;

alkylsulphinyl groups (R—SO—) wherein R is chosen from $C_1$-$C_4$ alkyl radicals;

alkylsulphonyl groups (R—SO$_2$—) wherein R is chosen from $C_1$-$C_4$ alkyl radicals;

nitro groups;

cyano groups;

halogen atoms;

thio groups (HS—); and alkylthio groups (RS—) wherein the radical R is chosen from optionally substituted $C_1$-$C_4$ alkyl radicals;

when e is 2, the two radicals $R_2$ may optionally form, with the carbon atoms to which they are attached, a secondary ring, aromatic or non-aromatic, comprising 5 or 6 ring members which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

e is an integer from 0 to 2; when e is less than 2, one or more unsubstituted carbon atom(s) of the heterocycle carry a hydrogen atom, the radicals $R_3$, which may be identical or different, are chosen from:

optionally substituted $C_1$-$C_{16}$ alkyl radicals optionally interrupted by at least one heteroatom or by at least one group comprising at least one heteroatom, hydroxyl groups, $C_1$-$C_4$ alkoxy groups, $C_2$-$C_4$ (poly)hydroxyalkoxy groups;

alkoxycarbonyl groups (RO—CO—) wherein R is chosen from $C_1$-$C_4$ alkyl radicals, alkylcarbonyloxy radicals (RCO—O—) wherein R is chosen from $C_1$-$C_4$ alkyl radicals;

alkylcarbonyl radicals (R—CO—) wherein R is chosen from $C_1$-$C_4$ alkyl radicals;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O and S and comprising 5 to 7 ring members, which is saturated or unsaturated, aromatic or non-aromatic and is optionally substituted;

alkylcarbonylamino group (RCO—NR'—) wherein the radical R is chosen from $C_1$-$C_4$ alkyl radicals and the radical R' is chosen from hydrogen and $C_1$-$C_4$ alkyl radicals;

aminocarbonyl group ((R)$_2$N—CO—) wherein the radicals R independently of one another are chosen from hydrogen and $C_1$-$C_4$ alkyl radicals;

ureido groups (N(R)$_2$—CO—NR'—) wherein the radicals R and R' independently of one another are chosen from hydrogen and $C_1$-$C_4$ alkyl radicals;

aminosulphonyl group ((R)$_2$N—SO$_2$—) wherein the radicals R independently of one another are chosen from hydrogen or a $C_1$-$C_4$ alkyl radicals;

alkylsulphonylamino groups (RSO$_2$—NR'—) wherein the radicals R and R' independently of one another are chosen from hydrogen and $C_1$-$C_4$ alkyl radicals;

thio groups (HS—);

alkylthio groups (RS—) wherein the radical R are chosen from $C_1$-$C_4$ alkyl radicals;

alkylsulphinyl groups (R—SO—) wherein R are chosen from $C_1$-$C_4$ alkyl radicals;

alkylsulphonyl groups (R—SO$_2$—) wherein R are chosen from $C_1$-$C_4$ alkyl radicals;

nitro groups;

cyano groups; and halogen atoms;

when m' is greater than or equal to 2, two adjacent radicals $R_3$ may form, with the carbon atoms to which they are attached, a secondary ring, aromatic or non-aromatic, comprising 6 ring members, which is optionally substituted by at least one group chosen from the following groups: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups or, amino groups substituted by one or two identical or different $C_1$-$C_4$ alkyl radicals which optionally carry at least one hydroxyl group, m' is an integer from 0 to 4; when m' is less than 4, then one or more unsubstituted carbon atom of the aromatic ring carry a hydrogen atom;

$W_1$ radicals, which are identical, are chosen from:

hydrogen, halogen atoms chosen from bromine, chlorine and fluorine,

—NR$_4$-Ph-NR$_5$R$_6$, —NR$_4$-Ph-OR$_7$, —O-Ph-OR$_7$ and —O-Ph-NR$_5$R$_6$ group, where:

$R_4$ and $R_7$, which may be identical or different, are chosen from hydrogen, optionally substituted $C_1$-$C_{20}$ alkyl radicals, optionally substituted aralkyl radicals and optionally substituted phenyl radicals;

$R_5$ and $R_6$, which may be identical or different, are chosen from hydrogen, optionally substituted $C_1$-$C_{20}$ alkyl radicals, optionally substituted phenyl radicals, optionally substituted aralkyl radicals, and an alkylcarbonyl radical (R—CO—) wherein R is a $C_1$-$C_4$ alkyl radical;

$R_5$ and $R_6$ may optionally form, with the nitrogen atom to which they are attached, a heterocycle comprising from 1 to 3 heteroatoms chosen from N, O and S and comprising 5 to 7 ring members, which is saturated or unsaturated, aromatic or non-aromatic and optionally substituted;

Ph is chosen from optionally substituted phenyl radicals;

—$NR_5$—$R_6$ groups, wherein $R_5$ and $R_6$, independently of each other, form, with the carbon atom of the aromatic ring adjacent to that to which —$NR_5R_6$ is attached, a 5- or 6-membered saturated heterocycle;

the radicals $R_1$, which may be identical or different, are chosen from:
optionally substituted $C_1$-$C_4$ alkyl radicals;
optionally substituted phenyl radicals; and
optionally substituted benzyl radicals;

L, a non-cationic linker connecting the two identical azo chromophores, is chosen from:
covalent bonds;
optionally substituted $C_1$-$C_{40}$ alkyl radicals optionally interrupted by a saturated or unsaturated, aromatic or non-aromatic (hetero)cycle comprising 3 to 7 ring members which are optionally substituted and optionally fused, the alkyls radical being optionally interrupted by at least one heteroatom or group comprising at least one heteroatom, with the proviso that the linker L not comprise an azo, nitro, nitroso or peroxo bonds;
optionally substituted phenyl radicals;

the electroneutrality of the compound of formula (I) being ensured by at least one identical or non-identical, cosmetically acceptable anions An, for a time sufficient to give the desired effect.

27. A device comprising a plurality of compartments, wherein a first compartment comprises a symmetrical cationic diazo compound chosen from those of formula (I) below, their resonance forms, and their acid addition salts and their solvates:

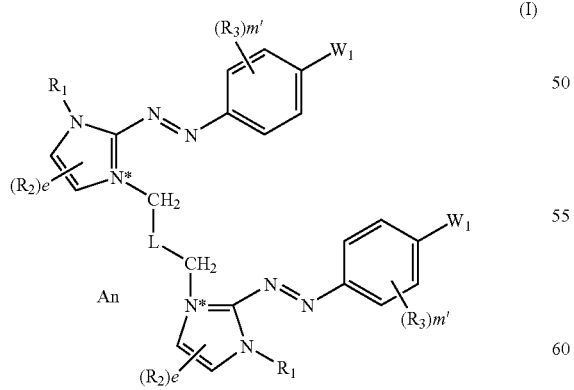

wherein:
the radicals $R_1$, which are identical or not, are chosen from:
optionally substituted $C_1$-$C_4$ alkyl radicals;
optionally substituted phenyl radicals; and
optionally substituted benzyl radicals;

the radicals $R_2$, which may be identical or different, are chosen from:
optionally substituted $C_1$-$C_{16}$ alkyl radicals optionally interrupted by at least one entity chosen from heteroatom and groups comprising at least one heteroatom, the alkyl radical being further optionally substituted by at least one group chosen from thio (—SH), $C_1$-$C_4$ thioalkyl; $C_1$-$C_4$ alkylsulphinyl or $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) wherein R is chosen from $C_1$-$C_4$ alkyl radicals,
alkylcarbonyloxy radicals (RCO—O—) wherein R is chosen from $C_1$-$C_4$ alkyl radicals,
alkylcarbonyl radicals (R—CO—) wherein R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O and S and 5 to 7 ring members, which is saturated or unsaturated, aromatic or non-aromatic and optionally substituted;
alkylcarbonylamino groups (RCO—NR'—) wherein the radical R is chosen from $C_1$-$C_4$ alkyl radicals and the radical R' is chosen from hydrogen and $C_1$-$C_4$ alkyl radicals;
aminocarbonyl groups (($R)_2$N—CO—) wherein the radicals R independently of one another are chosen from hydrogen and $C_1$-$C_4$ alkyl radicals;
ureido groups (N($R)_2$—CO—NR'—) wherein the radicals R and R' independently of one another are chosen from hydrogen and $C_1$-$C_4$ alkyl radicals;
aminosulphonyl groups (($R)_2$N—$SO_2$—) wherein the radicals R independently of one another are chosen from hydrogen and $C_1$-$C_4$ alkyl radicals;
alkylsulphonylamino groups ($RSO_2$—NR'—) wherein R is chosen from $C_1$-$C_4$ alkyl radicals and R' is chosen from hydrogen and $C_1$-$C_4$ alkyl radicals;
optionally substituted aryl radicals;
optionally substituted ($C_1$-$C_4$)alkylaryl radicals;
alkylsulphinyl groups (R—SO—) wherein R is chosen from $C_1$-$C_4$ alkyl radicals;
alkylsulphonyl groups (R—$SO_2$—) wherein R is chosen from $C_1$-$C_4$ alkyl radicals;
nitro groups;
cyano groups;
halogen atoms;
thio groups (HS—); and
alkylthio groups (RS—) wherein the radical R is chosen from optionally substituted $C_1$-$C_4$ alkyl radicals;
when e is 2, the two radicals $R_2$ may optionally form, with the carbon atoms to which they are attached, a secondary ring, aromatic or non-aromatic, comprising 5 or 6 ring members which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

e is an integer from 0 to 2; when e is less than 2, one or more unsubstituted carbon atom(s) of the heterocycle carry a hydrogen atom, the radicals $R_3$, which may be identical or different, are chosen from:
  optionally substituted $C_1$-$C_{16}$ alkyl radicals optionally interrupted by at least one heteroatom or by at least one group comprising at least one heteroatom, hydroxyl groups,
  $C_1$-$C_4$ alkoxy groups,
  $C_2$-$C_4$ (poly)hydroxyalkoxy groups;
  alkoxycarbonyl groups (RO—CO—) wherein R is chosen from $C_1$-$C_4$ alkyl radicals,
  alkylcarbonyloxy radicals (RCO—O—) wherein R is chosen from $C_1$-$C_4$ alkyl radicals;
  alkylcarbonyl radicals (R—CO—) wherein R is chosen from $C_1$-$C_4$ alkyl radicals;
  amino groups;
  amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O and S and comprising 5 to 7 ring members, which is saturated or unsaturated, aromatic or non-aromatic and is optionally substituted;
  alkylcarbonylamino group (RCO—NR'—) wherein the radical R is chosen from $C_1$-$C_4$ alkyl radicals and the radical R' is chosen from hydrogen and $C_1$-$C_4$ alkyl radicals;
  aminocarbonyl group ((R)$_2$N—CO—) wherein the radicals R independently of one another are chosen from hydrogen and $C_1$-$C_4$ alkyl radicals;
  ureido groups (N(R)$_2$—CO—NR'—) wherein the radicals R and R' independently of one another are chosen from hydrogen and $C_1$-$C_4$ alkyl radicals;
  aminosulphonyl group ((R)$_2$N—SO$_2$—) wherein the radicals R independently of one another are chosen from hydrogen or a $C_1$-$C_4$ alkyl radicals;
  alkylsulphonylamino groups (RSO$_2$—NR'—) wherein the radicals R and R' independently of one another are chosen from hydrogen and $C_1$-$C_4$ alkyl radicals;
  thio groups (HS—);
  alkylthio groups (RS—) wherein the radical R are chosen from $C_1$-$C_4$ alkyl radicals;
  alkylsulphinyl groups (R—SO—) wherein R are chosen from $C_1$-$C_4$ alkyl radicals;
  alkylsulphonyl groups (R—SO$_2$—) wherein R are chosen from $C_1$-$C_4$ alkyl radicals;
  nitro groups;
  cyano groups; and
  halogen atoms;
  when m' is greater than or equal to 2, two adjacent radicals $R_3$ may form, with the carbon atoms to which they are attached, a secondary ring, aromatic or non-aromatic, comprising 6 ring members, which is optionally substituted by at least one group chosen from the following groups: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups or, amino groups substituted by one or two identical or different $C_1$-$C_4$ alkyl radicals which optionally carry at least one hydroxyl group, m' is an integer from 0 to 4; when m' is less than 4, then one or more unsubstituted carbon atom of the aromatic ring carry a hydrogen atom;

$W_1$ radicals, which are identical, are chosen from:
  hydrogen,
  halogen atoms chosen from bromine, chlorine and fluorine,
  —NR$_4$-Ph-NR$_5$R$_6$, —NR$_4$-Ph-OR$_7$, —O-Ph-OR$_7$ and —O-Ph-NR$_5$R$_6$ group, where:
    $R_4$ and $R_7$, which may be identical or different, are chosen from hydrogen, optionally substituted $C_1$-$C_{20}$ alkyl radicals, optionally substituted aralkyl radicals and optionally substituted phenyl radicals;
    $R_5$ and $R_6$, which may be identical or different, are chosen from hydrogen, optionally substituted $C_1$-$C_{20}$ alkyl radicals, optionally substituted phenyl radicals, optionally substituted aralkyl radicals, and an alkylcarbonyl radical (R—CO—) wherein R is a $C_1$-$C_4$ alkyl radical;
    $R_5$ and $R_6$ may optionally form, with the nitrogen atom to which they are attached, a heterocycle comprising from 1 to 3 heteroatoms chosen from N, O and S and comprising 5 to 7 ring members, which is saturated or unsaturated, aromatic or non-aromatic and optionally substituted;
    Ph is chosen from optionally substituted phenyl radicals;
  —NR$_5$—R$_6$ groups, wherein $R_5$ and $R_6$, independently of each other, form, with the carbon atom of the aromatic ring adjacent to that to which —NR$_5$R$_6$ is attached, a 5- or 6-membered saturated heterocycle;

the radicals $R_1$, which may be identical or different, are chosen from:
  optionally substituted $C_1$-$C_4$ alkyl radicals;
  optionally substituted phenyl radicals; and
  optionally substituted benzyl radicals;

L, a non-cationic linker connecting the two identical azo chromophores, is chosen from:
  covalent bonds;
  optionally substituted $C_1$-$C_{40}$ alkyl radicals optionally interrupted by a saturated or unsaturated, aromatic or non-aromatic (hetero)cycle comprising 3 to 7 ring members which are optionally substituted and optionally fused, the alkyls radical being optionally interrupted by at least one heteroatom or group comprising at least one heteroatom, with the proviso that the linker L not comprise an azo, nitro, nitroso or peroxo bonds;
  optionally substituted phenyl radicals;

the electroneutrality of the compound of formula (I) being ensured by at least one identical or non-identical, cosmetically acceptable anions An, and a second compartment comprising an oxidizing composition.

* * * * *

UNITED STATES PATENT AND TRADEMARK OFFICE
CERTIFICATE OF CORRECTION

| | | |
|---|---|---|
| PATENT NO. | : 7,351,267 B2 | Page 1 of 1 |
| APPLICATION NO. | : 11/300300 | |
| DATED | : April 1, 2008 | |
| INVENTOR(S) | : Hervé David et al. | |

It is certified that error appears in the above-identified patent and that said Letters Patent is hereby corrected as shown below:

On the Title Page, and Column 1, line 3:

Item 54, title page, line 3, "LINKE" should read --LINKER--.

On the Title Page, after Item (60), "Related U.S. Application Data," and before Item (51), "Int. Cl.," insert the following missing data:

--(30)  Foreign Application Priority Data
 December 15, 2004        (FR)        04 53002--.

Signed and Sealed this

Nineteenth Day of August, 2008

JON W. DUDAS
*Director of the United States Patent and Trademark Office*